(12) United States Patent
Bortolozzo et al.

(10) Patent No.: US 9,975,603 B2
(45) Date of Patent: May 22, 2018

(54) BICYCLE ELECTRONIC SYSTEM AND RELATED METHOD

(71) Applicant: Campagnolo S.r.l., Vincenza (IT)

(72) Inventors: Gianluca Bortolozzo, Cavarzere (IT); Flavio Cracco, Vicenza (IT)

(73) Assignee: Campagnolo S.r.l., Vicenza (IT)

( * ) Notice: Subject to any disclaimer, the term of this patent is extended or adjusted under 35 U.S.C. 154(b) by 143 days.

(21) Appl. No.: 14/814,172

(22) Filed: Jul. 30, 2015

(65) Prior Publication Data

US 2016/0031527 A1 Feb. 4, 2016

(30) Foreign Application Priority Data

Aug. 1, 2014 (IT) ............................... MI2014A1410

(51) Int. Cl.
*B62M 25/08* (2006.01)
*A61B 5/18* (2006.01)
(Continued)

(52) U.S. Cl.
CPC ............... *B62M 25/08* (2013.01); *A61B 5/18* (2013.01); *B62M 9/122* (2013.01); *B62M 9/123* (2013.01); *B62M 9/132* (2013.01); *B62M 9/133* (2013.01); *B62J 2099/002* (2013.01); *B62J 2099/0013* (2013.01); *B62M 2025/003* (2013.01); *B62M 2025/006* (2013.01)

(58) Field of Classification Search
None
See application file for complete search history.

(56) References Cited

U.S. PATENT DOCUMENTS

| 6,047,230 A | 4/2000 | Spencer et al. |
| 2002/0180166 A1* | 12/2002 | Voss .................. B62J 99/00 280/5.5 |

(Continued)

FOREIGN PATENT DOCUMENTS

| CN | 103010390 A | 4/2013 |
| EP | 1473219 A1 | 11/2004 |

OTHER PUBLICATIONS

Italian Search Report and Written Opinion in Italian Application No. IT MI2014A001410, dated Mar. 24, 2015 with English translation.
(Continued)

*Primary Examiner* — Edwin A Young
(74) *Attorney, Agent, or Firm* — Volpe and Koenig, P.C.

(57) ABSTRACT

A method for actuating a bicycle electronic gearshift comprising the steps of: receiving a signal indicative of the heart rate of a cyclist using the bicycle; receiving a signal indicative of the power delivered by the cyclist; calculating a performance index as a function of the value of the signal indicative of the power and of the value of the signal indicative of the heart rate; obtaining a reference value for the performance index; comparing the calculated performance index with the reference value of the performance index; and, emitting a control signal as a function of the outcome of comparing step. A bicycle electronic system for practicing the disclosed method comprises an electronic gearshift, a heart rate monitor, a power sensor, and a controller configured to carry out each step of the method.

15 Claims, 16 Drawing Sheets

Figure 1:
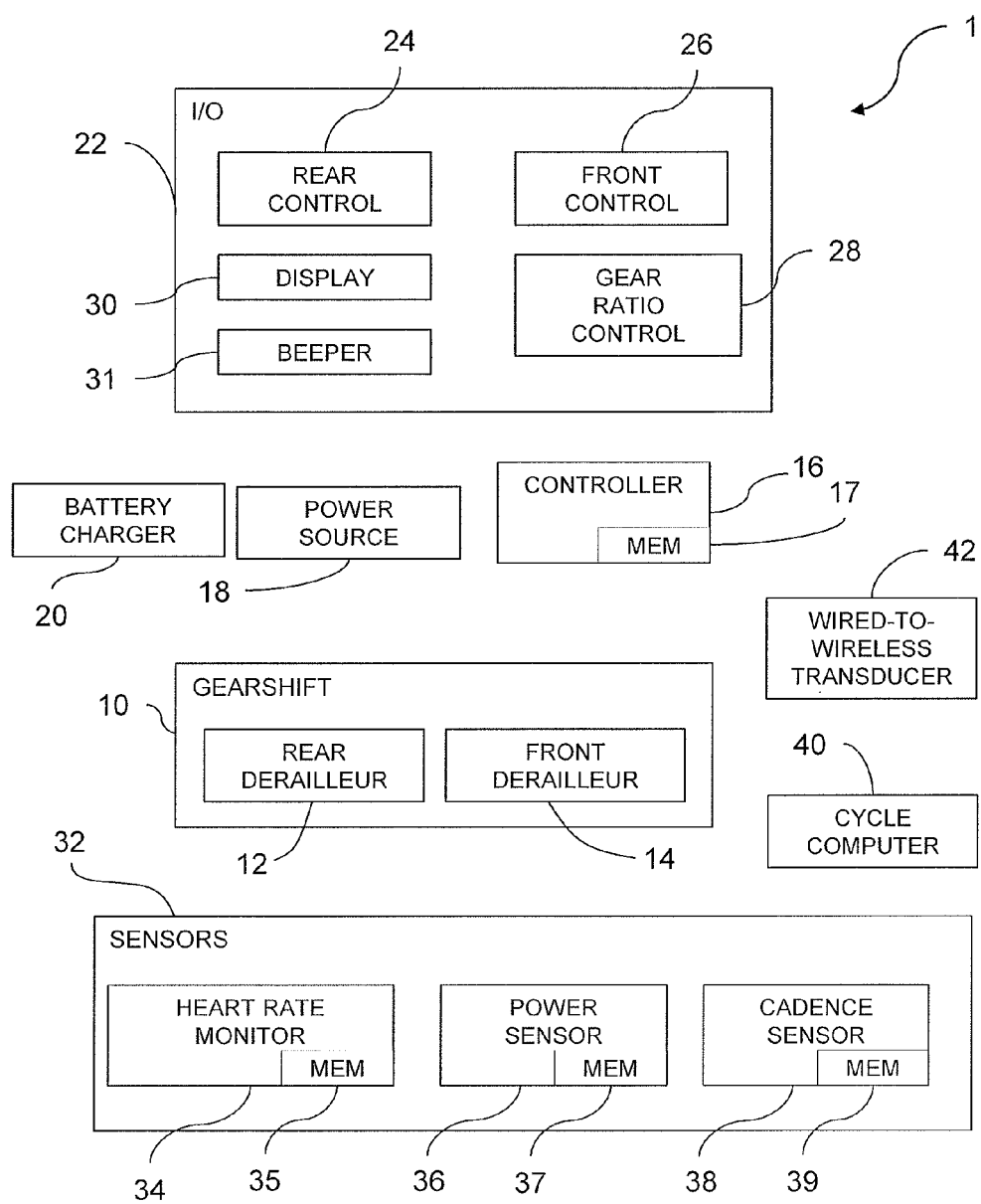

(51) Int. Cl.
 *B62M 9/122* (2010.01)
 *B62M 9/123* (2010.01)
 *B62M 9/132* (2010.01)
 *B62M 9/133* (2010.01)
 B62M 25/00 (2006.01)
 B62J 99/00 (2009.01)

(56) References Cited

U.S. PATENT DOCUMENTS

2009/0170660 A1\* 7/2009 Miglioranza ......... A63B 24/00
 482/1
2009/0181826 A1\* 7/2009 Turner .................... B62M 6/50
 482/4

OTHER PUBLICATIONS

Chinese Office Action for Application No. 201510468942.7, dated Oct. 26, 2017.

\* cited by examiner

BICYCLE ELECTRONIC SYSTEM AND RELATED METHOD

CROSS REFERENCE TO RELATED APPLICATION(S)

This application claims the benefit of Italian Application No. MI2014A001410, which was filed on Aug. 1, 2014, and is incorporated herein by reference as if fully set forth.

FIELD OF INVENTION

The present invention relates to a bicycle electronic system and in particular such a system including an electronic gearshift, as well as to a method for actuating a bicycle electronic gearshift.

BACKGROUND

A motion transmission system in a bicycle comprises a chain extending between toothed wheels associated with the axle of the pedal crank and with the hub of the rear wheel. When there is more than one toothed wheel at at least one of the axle of the pedal cranks and the hub of the rear wheel, and the motion transmission system is therefore provided with a gearshift, a front derailleur and/or a rear derailleur are provided for. In the case of an electronically servo-assisted gearshift, briefly called electronic gearshift herein, each derailleur comprises a chain guide element, also known as cage, movable to move the chain among the toothed wheels in order to change the gear ratio, and an electromechanical actuator to move the chain guide element. The actuator in turn typically comprises a motor, typically an electric motor, coupled with the chain guide element through a linkage such as an articulated parallelogram, a rack system or a worm screw system, as well as a sensor of the position, speed and/or acceleration of the rotor or of any moving part downstream of the rotor, down to the chain guide element itself. It is worthwhile noting that slightly different terminology from that used in this context is also in use.

The toothed wheels associated with the hub of the rear wheel are also known as sprockets, while those associated with the axle of the pedal cranks of the bicycle are also known as crowns or gears.

Control electronics changes the gear ratio automatically, for example based on one or more detected variables, such as the travel speed, the cadence of rotation of the pedal cranks, the torque applied to the pedal cranks, the slope of the travel terrain, the heart rate of the cyclist and similar, and/or the gear ratio is changed based on commands manually input by the cyclist through suitable control members, for example levers and/or buttons.

In gearshifts of a first type, a control device of the front derailleur and a control device of the rear derailleur—or only one of the two in the case of simpler gearshifts—are mounted so as to be easily manoeuvred by the cyclist, usually on the handlebars, close to the handgrips where the brake lever for controlling the brake of the front and rear wheel, respectively, is located. Control devices that allow driving both a derailleur in the two directions and a brake are commonly known as integrated controls. By convention, the control device of the front derailleur and the brake lever of the front wheel are located close to the left handgrip, and the control device of the rear derailleur and the brake lever of the rear wheel are located close to the right handgrip.

In gearshifts of a second type, a control device, again mounted so as to be easily manoeuvred by the cyclist, allows a gearshifting request manual command to be input—which can be to decrease the ratio or to increase the ratio—and the electronic system controls the driving of the front derailleur and/or of the rear derailleur to actuate the requested gearshifting.

The aforementioned components and possibly others are located on-board the bicycle and there are means for communication between them.

U.S. Pat. No. 6,047,230 discloses a bicycle gearshift system comprising a display, an interface to input manual commands, a sensor of the speed of the wheel, a cadence sensor, a gear changer position sensor, a sensor of the tension of a torque transmission member (chain), a clinometer, a sensor of the effort of the cyclist, a heart rate monitor, a drive rate sensor, a controller and a gear changer actuator. The controller generates a control signal based on the detected quantities. The gear changer actuator is coupled to the gear changer and moves it in response to the control signal positioning the torque transmission element with respect to a plurality of toothed wheels.

The system provides for a setting mode of characteristics of the bicycle and of characteristics of the cyclist, as well as various operating modes wherein the decisions on gearshifting are based selectively on constant cadence, constant pedalling force, constant acceleration, constant heart rate, a completely manual mode, a semi-automatic mode wherein manual controls prevail, and a mode based on artificial intelligence and in particular on fuzzy logic the decision parameters of which are the aforementioned detected quantities. The system also inhibits gearshifting if the speed of the wheel is too low or if the tension of the chain is too high.

As far as heart rate is concerned, the system provides that when the heart rate is less than a first threshold, the controller increases the gear ratio and when the heart rate is greater than a second threshold, the controller reduces the gear ratio, wherein preferably the first threshold is less than a target heart rate, that can be stored in the system, by a predetermined quantity, and the second threshold is greater than the target heart rate by a predetermined quantity. The document also notes, without providing any details, the fact that the system adjusts the target heart rate over time to account for warm-up and cool-down intervals.

The invention provides a bicycle electronic system and a method for actuating a bicycle electronic gearshift that provide at least one operating mode that is particularly effective in terms of training.

SUMMARY OF THE INVENTION

In particular, the invention aims to provide a bicycle electronic system and a method for actuating a bicycle electronic gearshift that allow changes of gear ratio to be carried out based on the feedback obtained by plural sensors, in order to optimize the cyclist's performance.

Preferably, the invention also aims to allow particularly efficient and effective use of the bicycle with various gearshifting profiles linked to the type of athletic activity desired.

BRIEF DESCRIPTION OF THE DRAWING(S)

Figure 2:
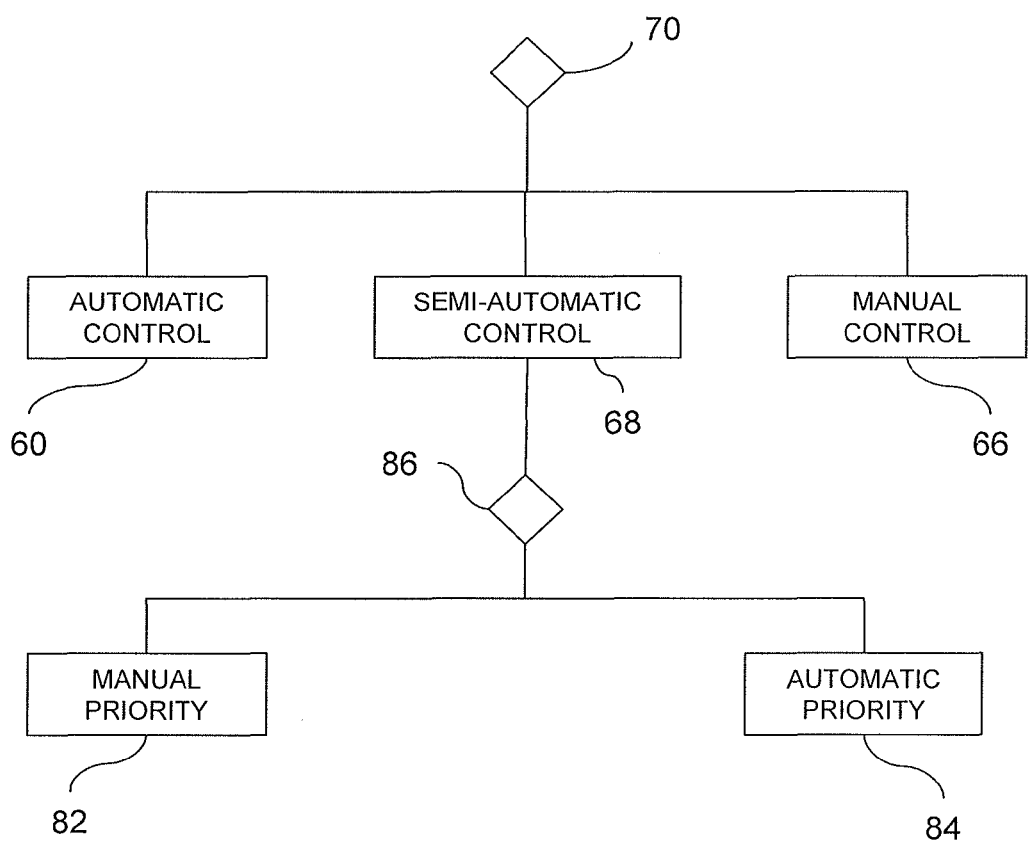
Figure 3:
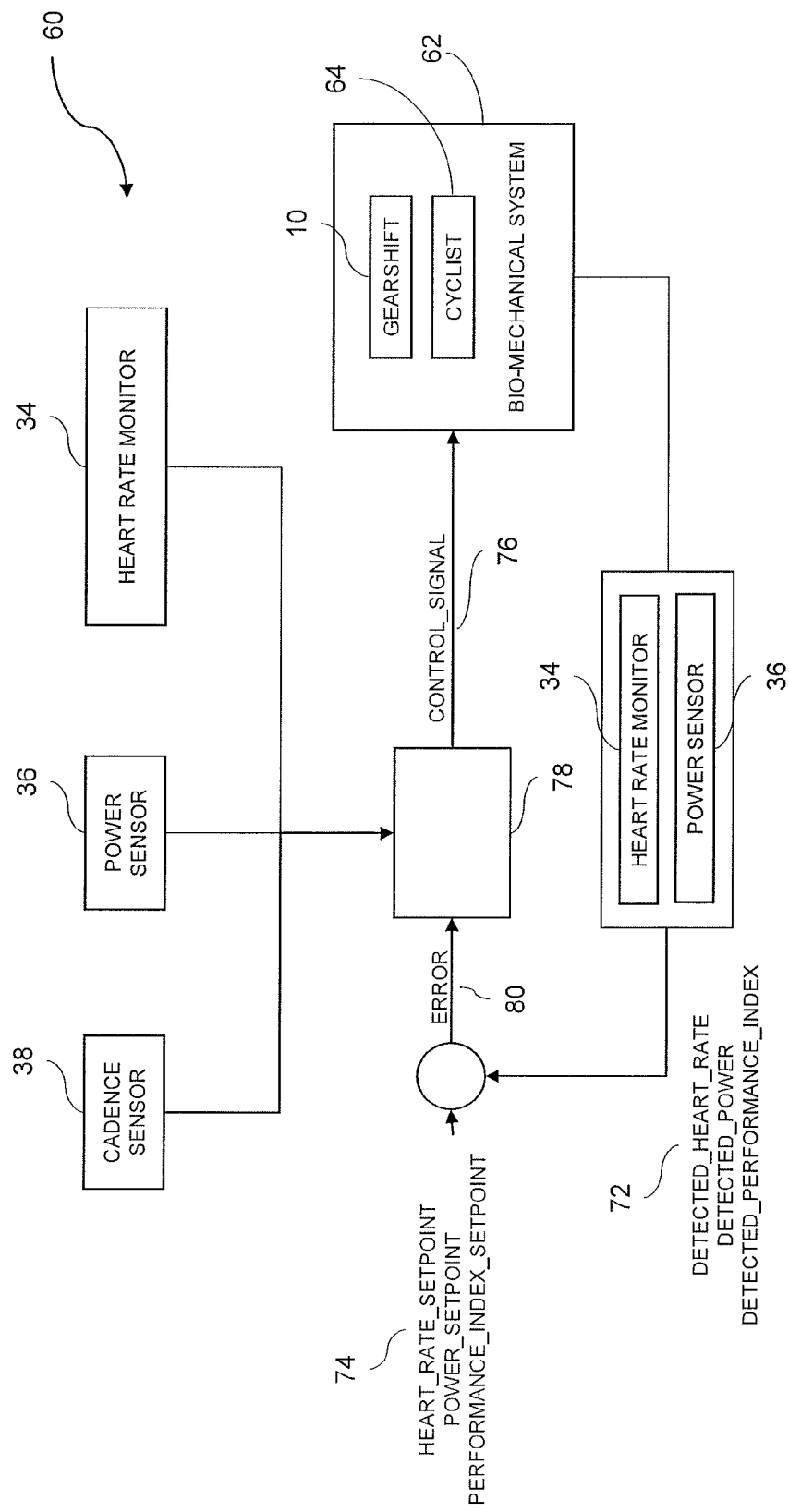
Figure 4:
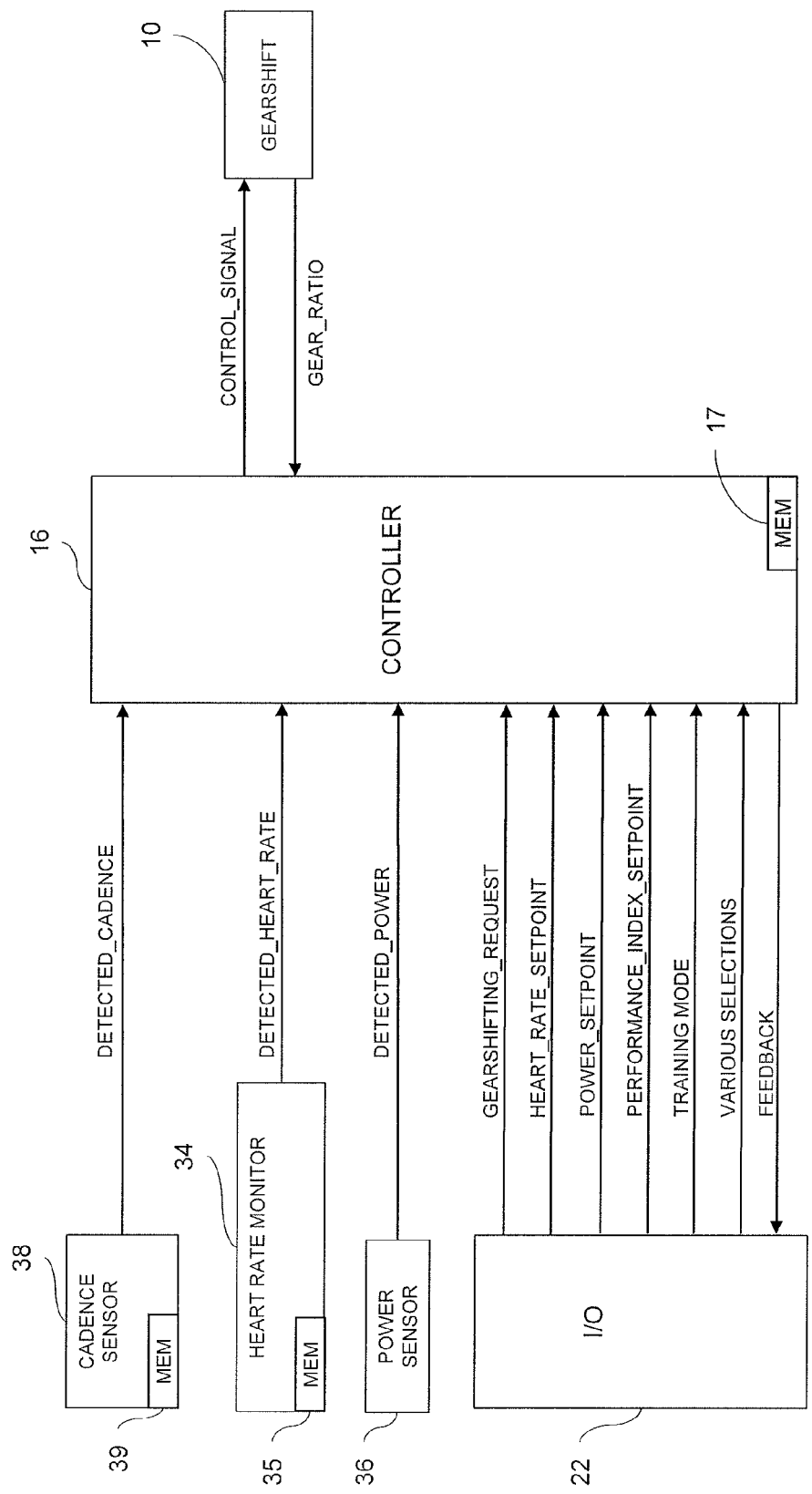
Figure 5:
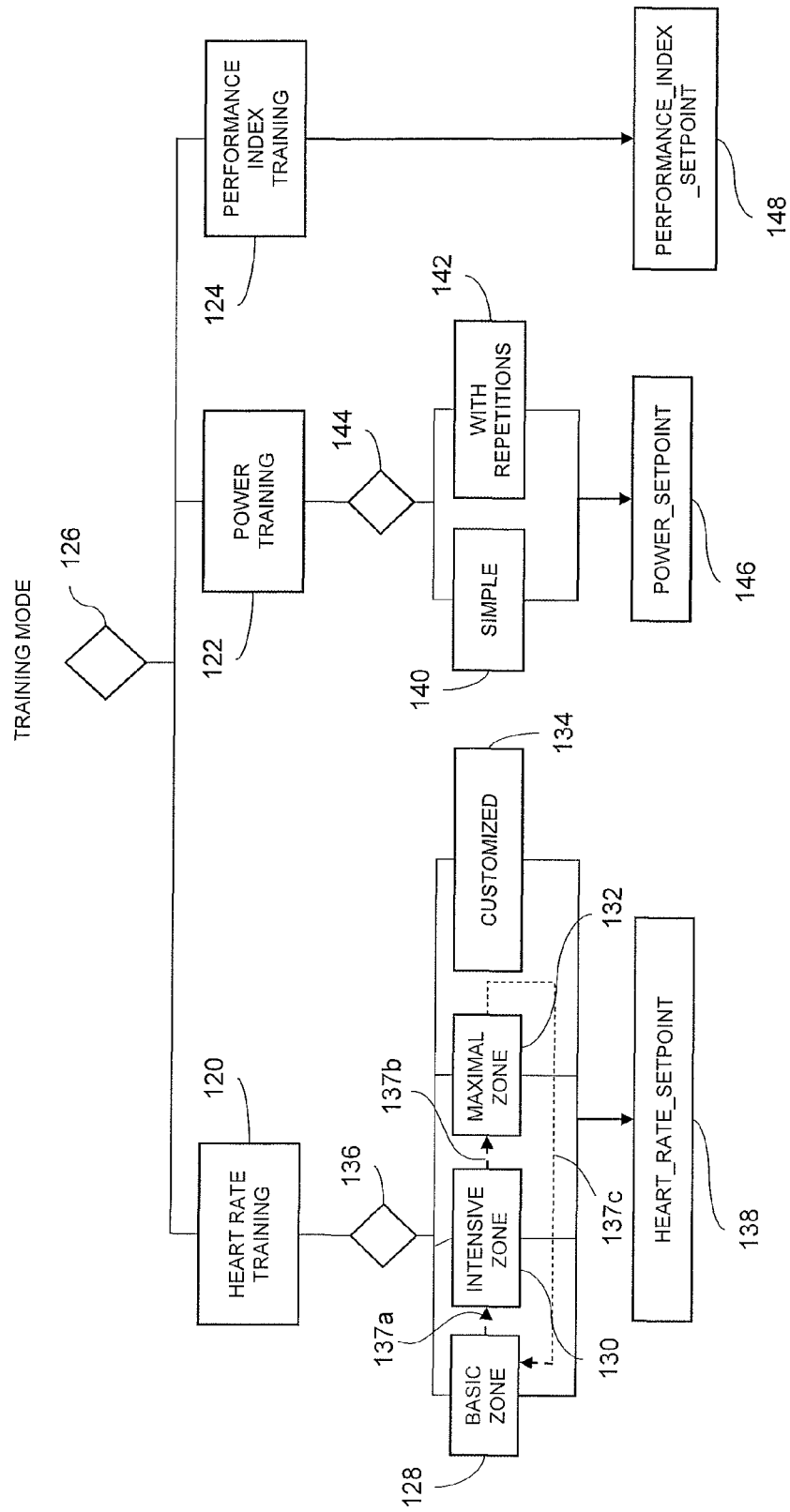
Figure 6:
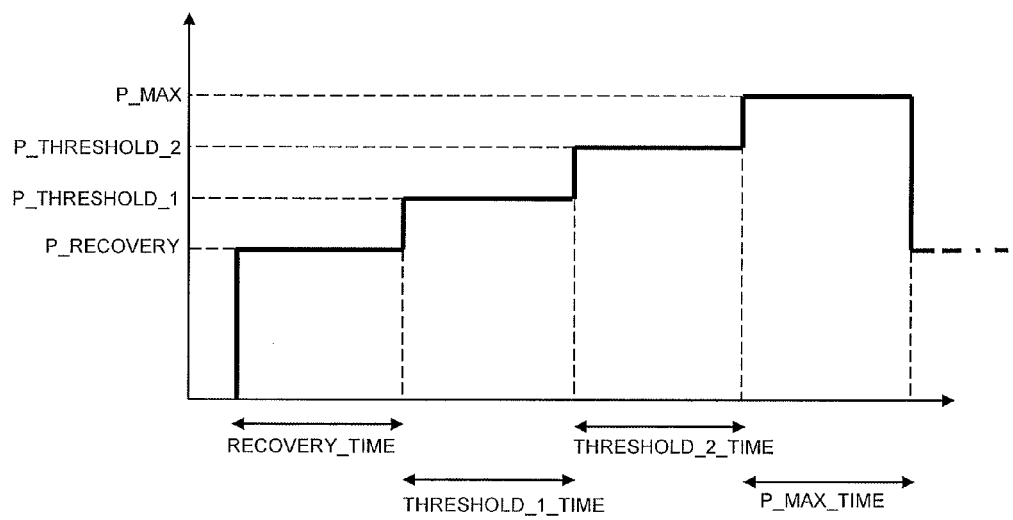
Figure 8:
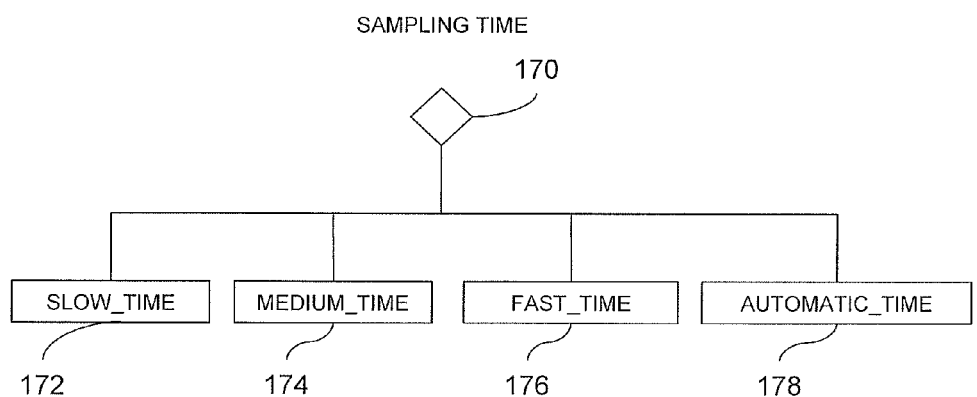
Figure 7:
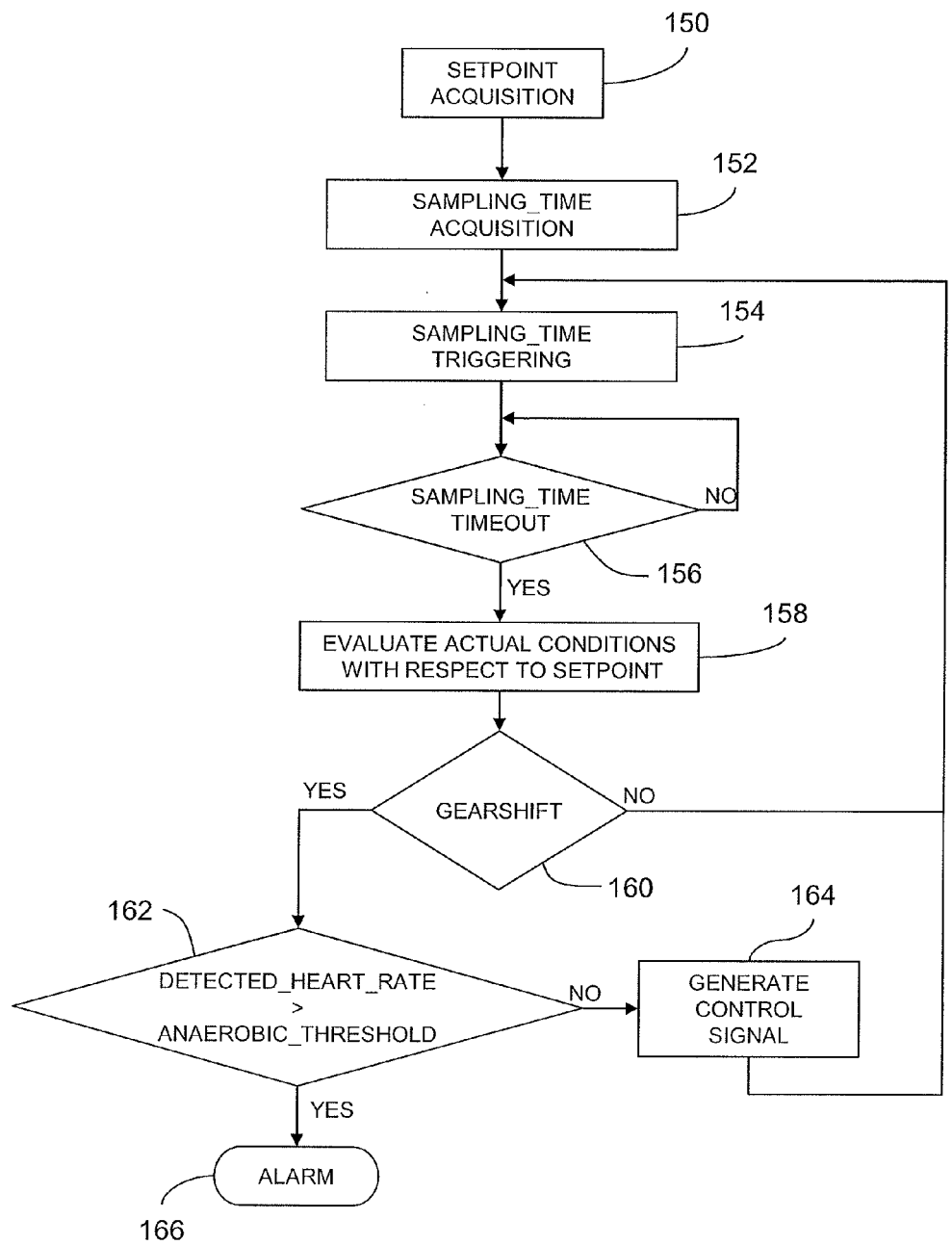
Figure 11:
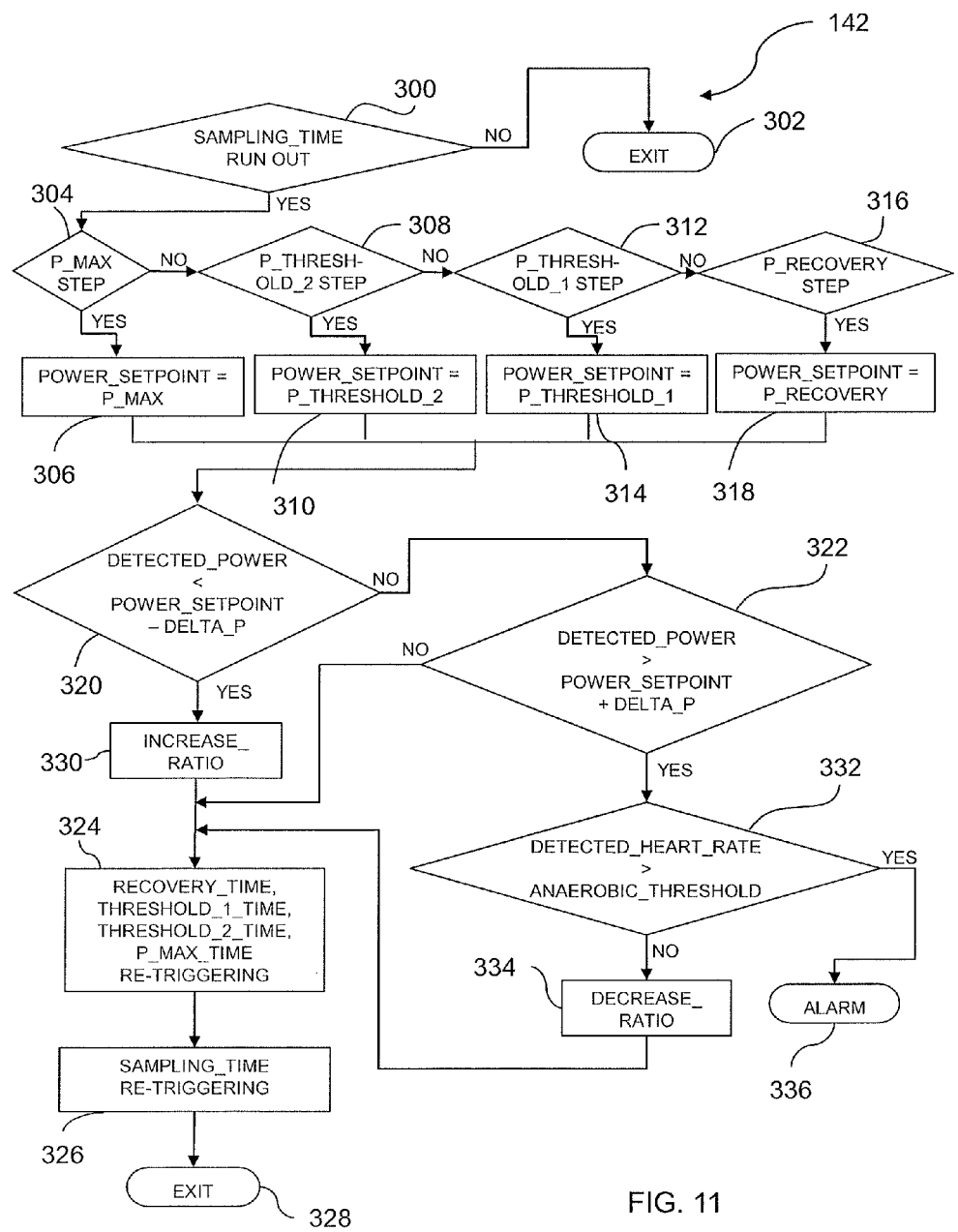
Figure 12:
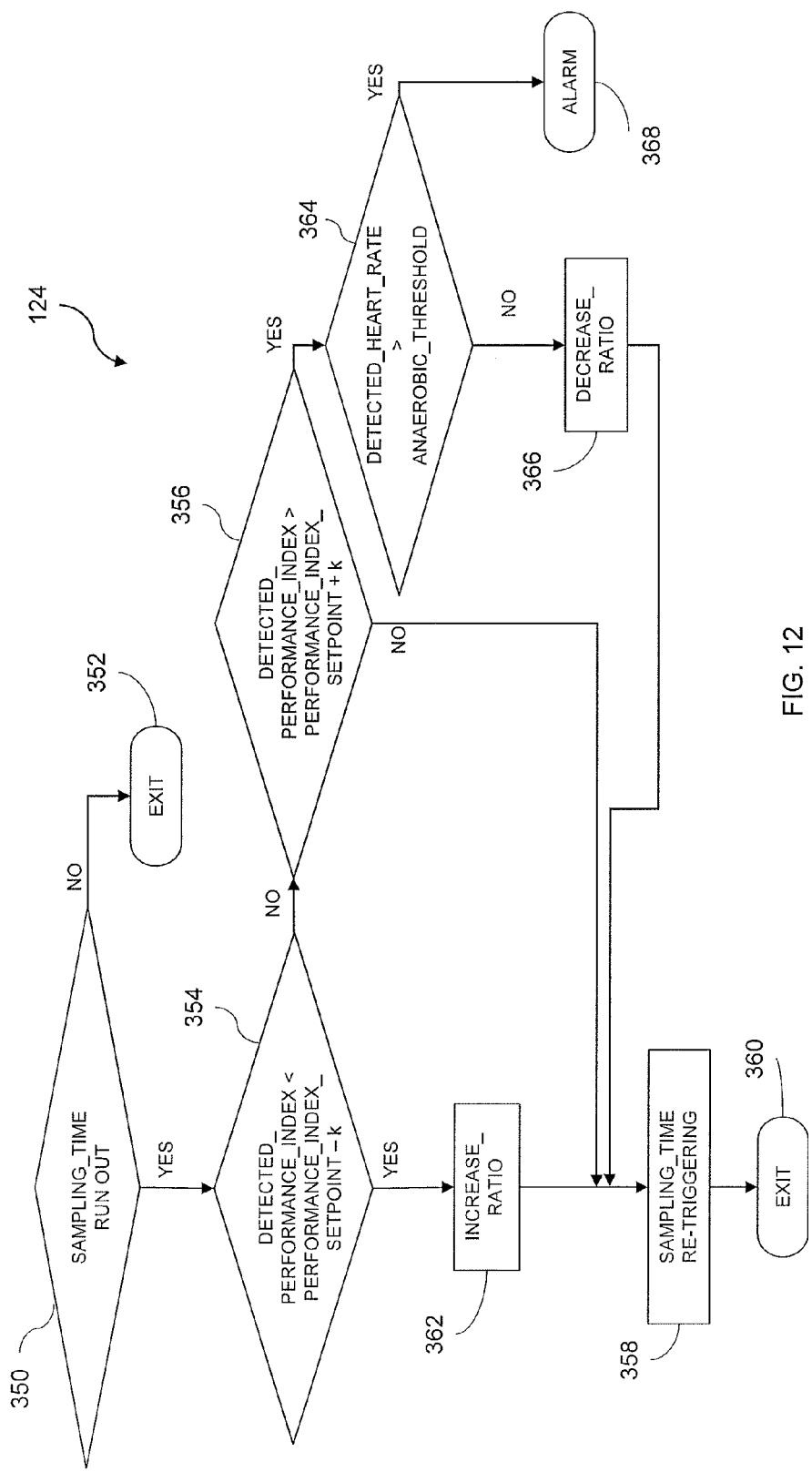
Figure 13:
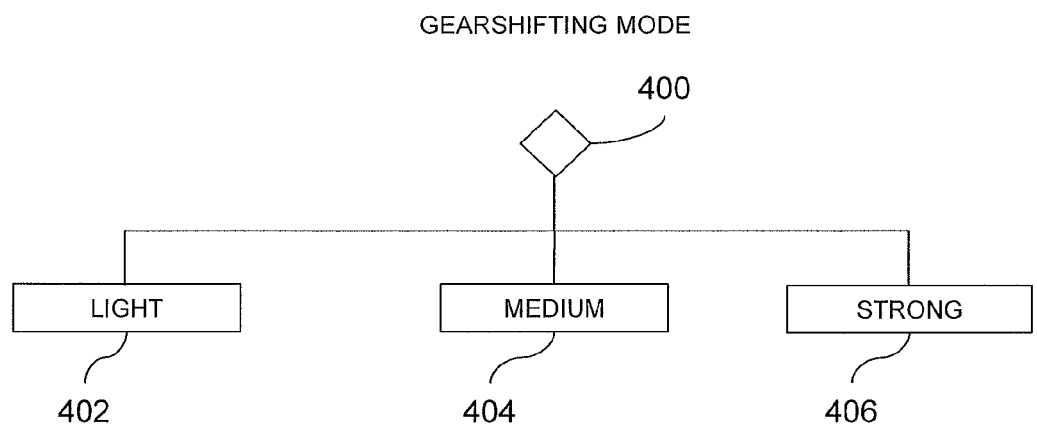
Figure 14A:
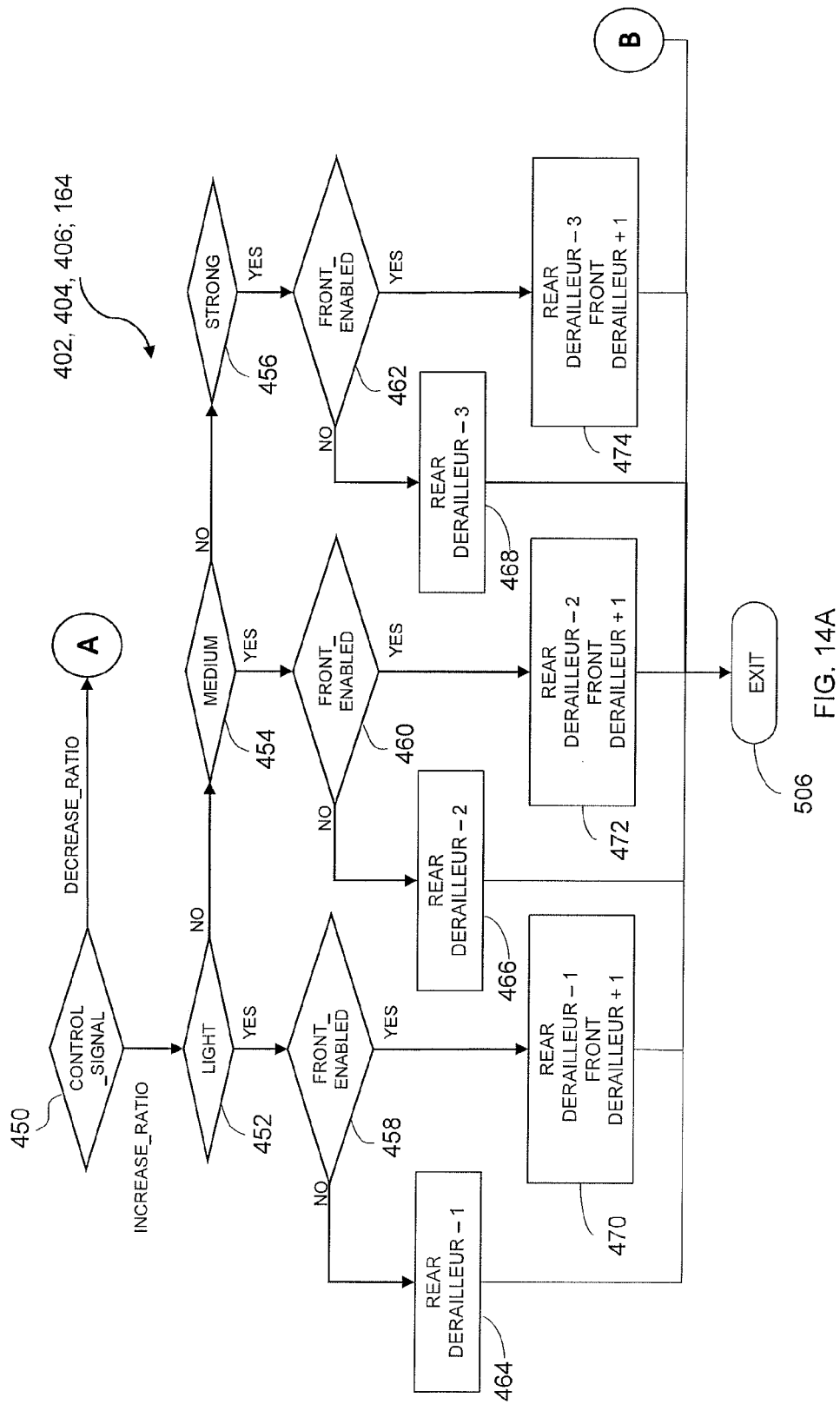
Figure 14B:
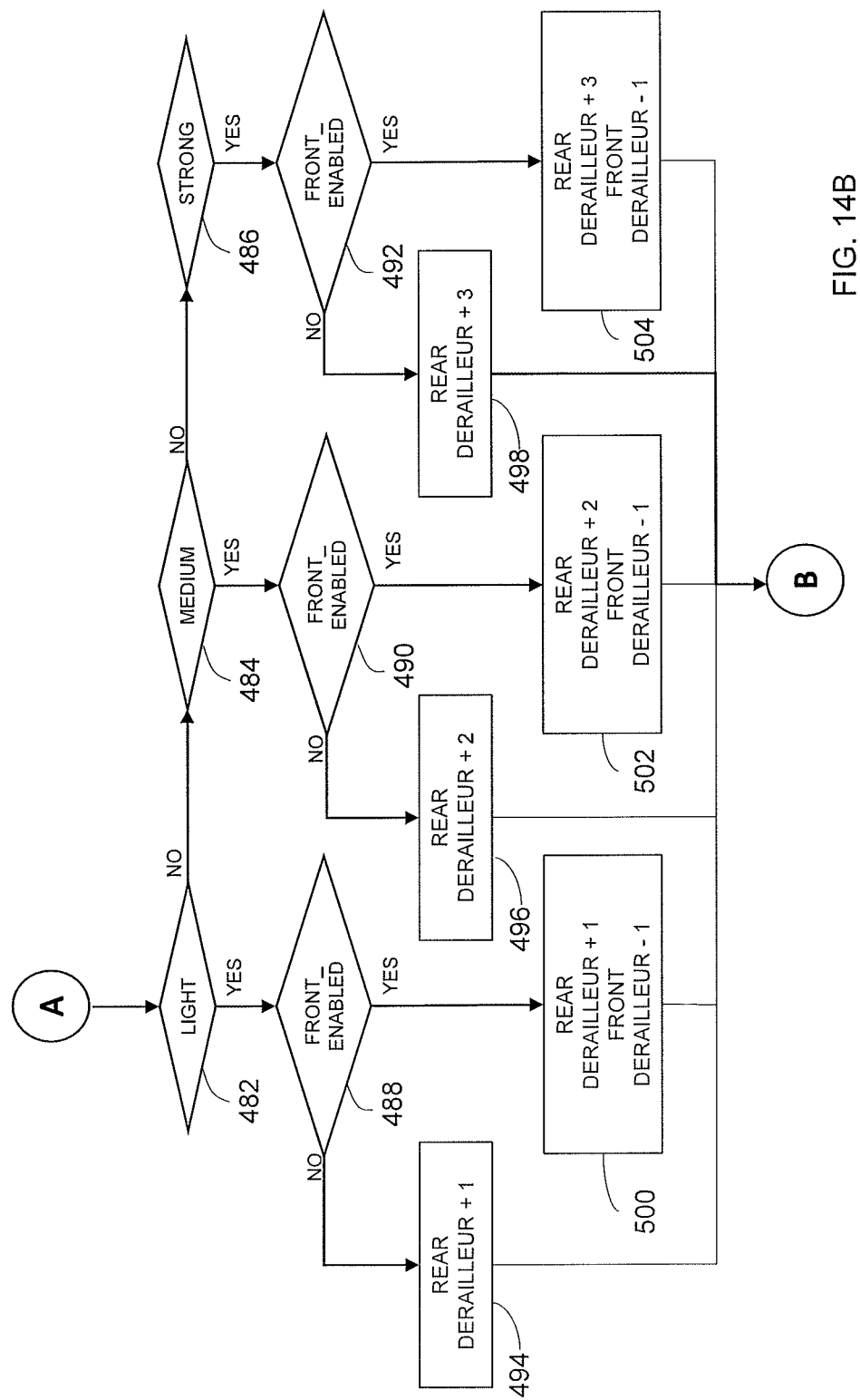
Figure 15:
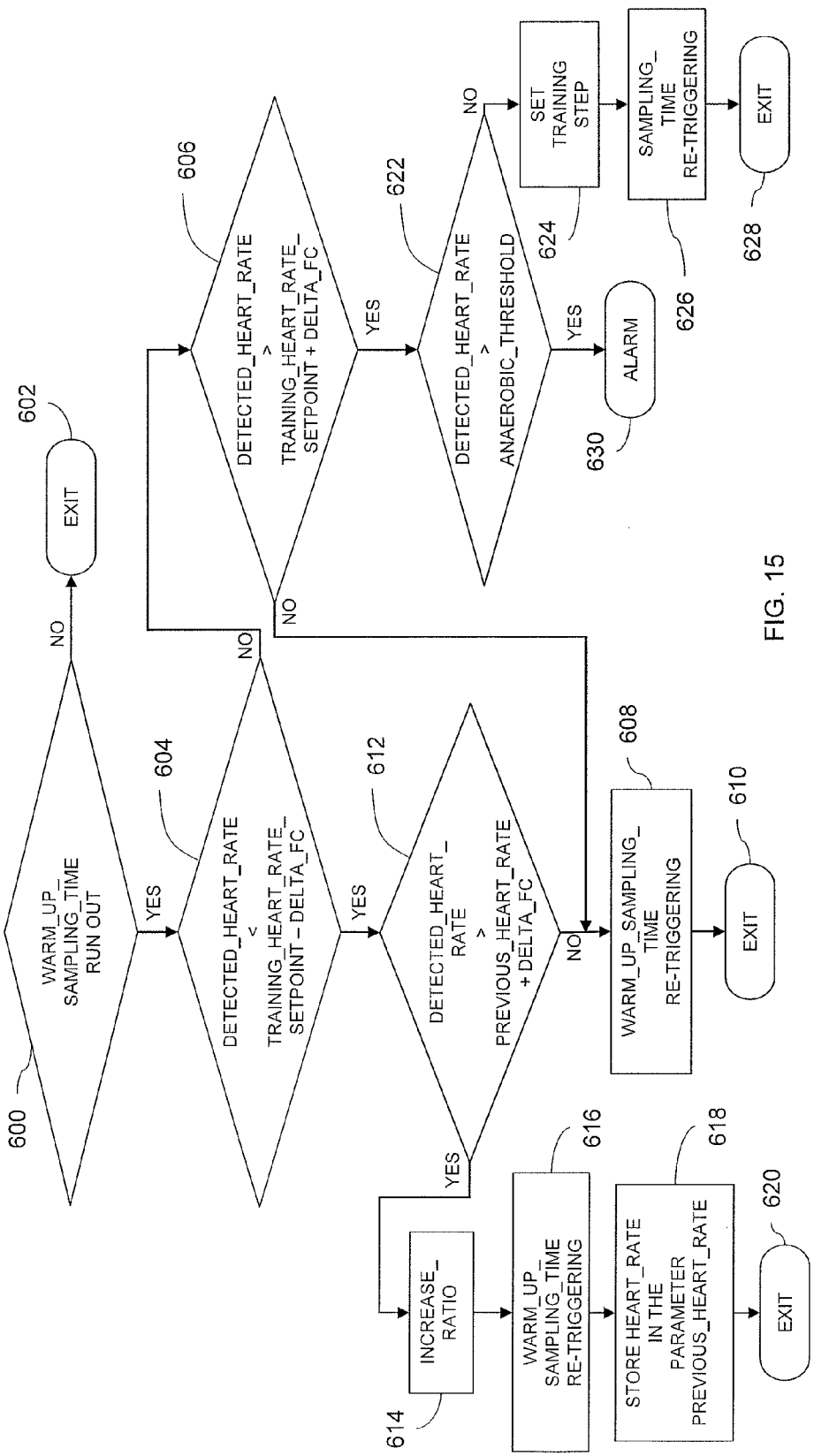
Figure 16:
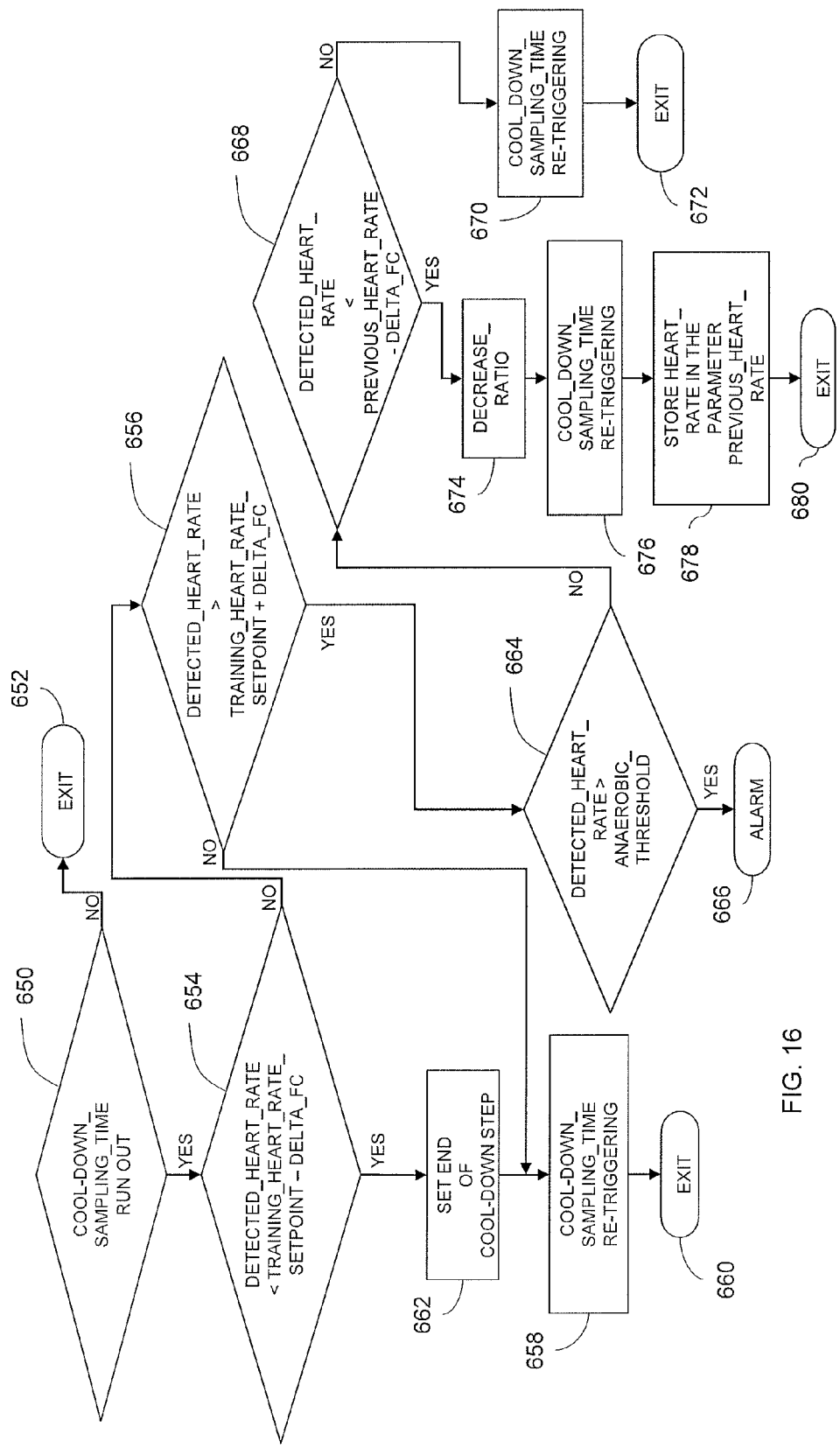

Features and advantages of the present invention will become clearer from the following detailed description of some preferred embodiments thereof, made with reference to the attached drawings. The different features illustrated and described with reference to the individual configurations can be combined together as desired. In the following description, in order to illustrate in the figures identical or similar reference numbers are used to indicate constructive or functional elements with the same function or an analogous function. In the drawings:

FIG. 1 is a block diagram of a bicycle electronic system according to an embodiment of the present invention, FIG. 2 diagrammatically represents various control modes of a gearshift according to the invention, FIG. 3 diagrammatically represents an automatic control of a gearshift according to the invention, FIG. 4 is a functional block diagram that illustrates the exchange among the main components of a bicycle electronic system according to the invention of the values of the main parameters, quantities and/or variables that intervene in the method for actuating the gearshift of the invention, FIG. 5 schematically represents various training modes according to the invention, FIG. 6 is a power vs. time diagram relating to a specific training mode according to the invention, FIG. 7 is a flow chart relating to the actuation method of the invention, FIG. 8 diagrammatically represents various sampling times provided for according to the invention, FIGS. 9-12 are flow charts relating to various training modes according to the invention, FIG. 13 diagrammatically represents various gearshifting modes provided for according to the invention, FIG. 14 is a flow chart relating to gearshifting according to the invention, made on two sheets as FIG. 14A and FIG. 14B, FIG. 15 is a flow chart relating to a warm-up mode according to the invention, and FIG. 16 is a flow chart relating to a cool-down mode according to the invention.

DETAILED DESCRIPTION OF THE INVENTION

Introduction

In an aspect thereof, the present invention relates to a method for actuating a bicycle electronic gearshift, comprising the steps of:

(a) receiving a signal indicative of the heart rate of a cyclist using the bicycle, (b) receiving a signal indicative of the power delivered by the cyclist, (c) calculating a performance index as a function of the value of the signal indicative of the power and of the value of the signal indicative of the heart rate, (d) obtaining a reference value for the performance index, (e) comparing the calculated performance index with the reference value of the performance index, (f) emitting a control signal of a gearshift as a function of the outcome of the comparing step.

Said steps are carried out in an electronic controller of the bicycle gearshift.

Preferably step (c) comprises calculating the performance index as a ratio between the value of the signal indicative of the power and the value of the signal indicative of the heart rate.

For the sake of simplicity of explanation, hereinafter reference will solely be made to a performance index calculated as a ratio between the aforementioned variables, but this must not be construed in the limiting sense and more complex or in any case different calculation expressions can be used.

Preferably, step (e) comprises checking whether the calculated performance index is below the lower limit of a reference area about the reference value of the performance index, and:

in the affirmative case, step (f) comprises emitting a signal to increase a gear ratio of the gearshift;

in the negative case, step (f) comprises emitting a signal to reduce a gear ratio of the gearshift.

Preferably, the method comprises the step of:

(g) checking whether the value of the signal indicative of the heart rate is above a threshold value indicative of the anaerobic threshold of the cyclist, and the step (f) of emitting a control signal of a gearshift is carried out only if the check of step (g) has a negative outcome, while if the check of step (g) has a positive outcome, the method comprises the step of:

(h) activating an alarm mode.

Preferably step (g) of checking whether the value of the signal indicative of the heart rate is above the threshold value indicative of the anaerobic threshold of the cyclist further comprises checking whether it remains above the threshold value for a predetermined minimum time period.

Preferably, step (h) of activating an alarm mode comprises emitting a signal to reduce a gear ratio of the gearshift.

Preferably, step (h) of activating an alarm mode comprises keeping the new gear ratio of the gearshift for a predetermined time period.

Preferably said steps (a)-(f) are carried out at a sampling frequency selectable among at least two different values.

Preferably, the method comprises the step of:

(i) selecting the sampling frequency based on the signal indicative of the heart rate of the cyclist using the bicycle and/or on the signal indicative of the power delivered by the cyclist.

Preferably, the bicycle gearshift comprises a rear derailleur and a front derailleur, wherein the method comprises the steps of:

(j) selectively enabling or disabling the movement of the front derailleur, and (k) actuating the control signal through a movement of the rear derailleur and/or a movement of the front derailleur in the case in which the movement of the front derailleur is enabled in step (j), through a movement of only the rear derailleur in the case in which the movement of the front derailleur is disabled in step (j).

Preferably, in a default mode, the movement of the front derailleur is disabled.

Preferably, the method further comprises the step of indicating to the cyclist when the front derailleur is enabled and/or indicating gearshifting of the front derailleur in progress.

Preferably, the method comprises the steps of:

(l) receiving a gearshifting request signal from a user interface, (m) in a semi-automatic mode, step (f) comprises emitting a control signal of the gearshift as a function of the outcome of comparing step (e) and/or based on the gearshifting request signal received in step (l).

Preferably, in a default mode the control signal of the gearshift is emitted giving priority to the outcome of comparing step (e).

Preferably the method comprises the step of checking whether the signal indicative of the heart rate and the signal indicative of the delivered power are correctly received in step (a) and in the affirmative case, inhibiting the sending of the gearshifting request signal from the user interface, in the negative case, switching to a mode wherein the control signal of the gearshift is emitted based on, or giving priority to, the gearshifting request signal received from the user interface.

Preferably, the step of checking whether the signal indicative of the heart rate and the signal indicative of the delivered power are correctly received in step (a) comprises checking whether they are received with a predetermined minimum periodicity and/or whether they are updated with a predetermined minimum periodicity.

Preferably, step (d) comprises:

(d1) generating the reference value for the performance index with a stepped progression.

More preferably, step (d1) comprises:

(d2) generating the reference value for the performance index with a stepped progression that repeats cyclically.

Preferably, the method comprises the step of:

(n) selecting from at least two gearshifting modes selected among a light gearshifting mode, a medium gearshifting mode, a strong gearshifting mode, and wherein if the preselected gearshifting mode is light gearshifting mode, step (f) of emitting a control signal of the gearshift comprises emitting a request signal for changing the gear ratio into the closest one among those available—the immediately greater one or the immediately smaller one, respectively;

if the preselected gearshifting mode is medium gearshifting mode, step (f) of emitting a control signal of the gearshift comprises emitting a request signal for changing the gear ratio into the second closest one among those available the second greater one or the second smaller one, respectively;

if the preselected gearshifting mode is strong gearshifting mode, step (f) of emitting a control signal of the gearshift comprises emitting a request signal for changing the gear ratio into the third closest one among those available—the third greater one or the third smaller one, respectively.

In an aspect the invention relates to a method for actuating a bicycle electronic gearshift, comprising the steps of:

(a) receiving at least one detected variable of a system comprising the bicycle gearshift and a cyclist using the bicycle, (b) obtaining at least one reference value for said at least one detected variable, (c) comparing said at least one detected variable with said at least one reference value, and (d) emitting a control signal of the gearshift based on the outcome of comparing step (c), wherein the method further comprises the step of (e) receiving a signal indicative of the heart rate of the cyclist using the bicycle, as at least part of step (a) or as an additional step to step (a), (f) checking whether the value of the signal indicative of the heart rate is above a threshold value indicative of the anaerobic threshold of the cyclist, and wherein step (d) of emitting a control signal of the gearshift is carried out only if the check of step (f) has a negative outcome, while if the check of step (f) has a positive outcome, the method comprises the step of:

(g) activating an alarm mode.

Preferably, step (a) comprises step (e).

Alternatively or in addition thereto, step (a) comprises the step of receiving a signal indicative of the power delivered by the cyclist.

Alternatively or in addition thereto, step (a) comprises: step (e) and/or the step of receiving a signal indicative of the power delivered by the cyclist and/or the step of receiving a performance index, relative to which what stated above applies.

In an aspect the invention relates to a method for actuating a bicycle gearshift, comprising the steps of:

(a) receiving at least one detected variable of a system comprising the bicycle gearshift and a cyclist using the bicycle, (b) emitting a control signal of the gearshift based on said at least one detected variable, said steps (a) and (b) being carried out at a sampling frequency, wherein the method further comprises the step of:

(c) selecting the sampling frequency from at least two different values.

In an aspect the invention relates to a method for actuating a bicycle gearshift having a rear derailleur and a front derailleur, comprising the steps of:

(a) receiving at least one detected variable of a system comprising the bicycle gearshift and a cyclist using the bicycle, (b) emitting a control signal of the gearshift based on said at least one detected variable, (c) actuating the control signal through a movement of the rear derailleur and/or a movement of the front derailleur, wherein said method further comprises (d) selectively enabling or disabling the movement of the front derailleur.

In an aspect, the invention relates to a method for actuating a bicycle gearshift, comprising the steps of:

(a) receiving at least one detected variable of a system comprising the bicycle gearshift and a cyclist using the bicycle, (b) evaluating said at least one detected variable, (c) receiving a gearshifting request signal of a user interface, (d) in a semi-automatic mode, emitting a control signal of the gearshift based on the gearshifting request signal and/or based on the outcome of step (b) of evaluating the at least one detected variable, wherein in a default mode, the control signal of the gearshift is emitted giving priority to the outcome of step (b) of evaluating the at least one detected variable.

Preferably, the method comprises the step of checking whether said at least one detected variable is correctly received in step (a), and in the affirmative case, inhibiting the sending of said gearshifting request signal from said user interface, in the negative case, switching to a mode wherein the control signal of the gearshift is emitted based on, or giving priority to, the gearshifting request signal received of the user interface.

Preferably, the step of checking whether said at least one detected variable is correctly received comprises checking whether the detected variable is received with a predetermined minimum periodicity and/or whether it is updated with a predetermined minimum periodicity.

In an aspect, the invention relates to a method for actuating a bicycle gearshift, comprising the steps of:

(a) receiving a signal indicative of the power delivered by the cyclist, (b) receiving a reference value for the power signal, (c) comparing the signal indicative of the power with the reference value, (d) emitting a control signal of the gearshift as a function of the outcome of comparing step (c), wherein the method further comprises the step of:

(e) generating the value of said reference value with a stepped progression.

Preferably, step (e) comprises generating the value of said reference value with a stepped progression that repeats cyclically.

More preferably, step (e) comprises generating the value of said reference value with a stepped progression, each step with a constant reference value and each with a predetermined duration.

In an aspect, the invention relates to a method for actuating a bicycle gearshift, comprising the steps of:

(a) receiving at least one detected variable of a system comprising the bicycle gearshift and a cyclist using the bicycle, (b) emitting a control signal of the gearshift based on said at least one detected variable, wherein the method further comprises the step of (c) selecting from at least two gearshifting modes selected among a light gearshifting mode, a medium gearshifting mode, a strong gearshifting mode, and wherein:

if said preselected gearshifting mode is light gearshifting mode, said step (b) of emitting a control signal of the gearshift comprises emitting a request signal for changing the gear ratio into the closest one among those available—the immediately greater one or the immediately smaller one, respectively;

if said preselected gearshifting mode is medium gearshifting mode, said step (b) of emitting a control signal of the gearshift comprises emitting a request signal for changing the gear ratio into the second closest one among those available—the second greater one or the second smaller one, respectively;

if said preselected gearshifting mode is strong gearshifting mode, said step (b) of emitting a control signal of the gearshift comprises emitting a request signal for changing the gear ratio into the third closest one among those available—the third greater one or the third smaller one, respectively.

Secondary aspects of the first method outlined above have advantageous application, mutatis mutandis, also in the other methods outlined above.

In an aspect, the invention relates to a bicycle electronic system comprising an electronic gearshift, a controller, a heart rate monitor and a power sensor, wherein the controller comprises modules adapted to carry out the steps of one or more of the methods outlined above.

PREFERRED EMBODIMENT(S)

With reference to FIG. 1, a bicycle electronic system 1 comprises one or more of the various mechanical, electromechanical and electronic components described hereinafter. It should be emphasized that not all of the components illustrated and described are necessarily present in the system 1, some being optional or provided as alternatives to each other, as will be apparent to those skilled in the art. The components are housed in one or more casings, each casing being more or less stably fixable to the bicycle and/or worn by the cyclist.

The system 1 comprises a gearshift 10. The gearshift 10 comprises a rear derailleur 12 and/or a front derailleur 14. For the description of these electromechanical components, which are per se known, reference is made to the background and introduction above.

The system 1 typically comprises a controller 16. The controller 16 comprises at least one processor—typically a microprocessor or a microcontroller—suitable for implementing one or more of the steps of the method described herein, by providing for suitable procedures and/or hardware, software and/or firmware modules.

In the present description and in the attached claims, therefore, under the term controller 16 a logic unit shall be meant, which can however be formed from plural physical units, in particular from one or more distributed microprocessors that can be contained in one or more casings together with one or more of the other components of the system 1.

The controller 16 is provided with an internal memory 17 for the volatile and/or non-volatile storage of program instructions, parameters, variables and constants. Alternatively or in addition thereto, the controller can communicate with an external memory (not shown).

In the rest of the description reference will be made mainly to modules, functions, algorithms and/or procedures implemented in the system 1 and in particular by the controller 16, but it should be understood that such a description also applies as a description of corresponding steps of an actuation method of an electronic gearshift and vice-versa.

The system 1 or, respectively, the actuation method according to the invention, described hereinafter, use a plurality of parameters and variables, the values of which are preferably stored in the memory 17. Such parameters and variables will be mentioned one at a time during the course of the following description.

In order to monitor the elapsing of predetermined time periods, also called timing periods, the controller 16 manages one or more timers—which can be a dedicated device or a software/firmware/hardware function. The timer can be made in any known way, for example through a variable linked to the clock of the controller 16, and it can be of the incremental- (stopwatch) or countdown-type. This happens in a way that is per se well known to a skilled in the art and as such it is not described herein in detail. Hereinafter, the expression "trigger" and derived forms will be used to indicate the zeroing operation in the case of an incremental timer, or the operation of resetting the maximum value in the case of a countdown timer, and the expression "run out" of the timer and derived forms will be used to indicate that the maximum value has been reached in the case of an incremental timer or that zero has been reached in the case of a countdown timer. Hereinafter, for the sake of brevity, reference will also be made directly to the trigging/running out of the time period monitored by the timer.

The system 1 comprises a power source 18. The power source 18 typically comprises at least one rechargeable battery. Alternatively or in addition thereto, the power source 10 can comprise a dynamo that generates electrical energy in the form of direct current from the mechanical work of rotation of a wheel of the bicycle. In practice, there can be plural power sources located in the system 1, also of different types, for example a power source for moving the derailleur(s) and at least one power source suitable for the electronic components.

Preferably, the rechargeable battery is of the "smart" type, namely provided with a dedicated control microprocessor, with a memory of battery data such as optimal operating parameters, charging/discharging cycles, remaining charge, etc.

In the case in which the power source 18 comprises at least one rechargeable battery, the system 1 can comprise a battery charger 20, preferably of the "smart" type.

The system 1 comprises a user interface 22. The user interface 22 typically comprises at least one electromechanical manual control device 24, 26, 28 as discussed in the introductory part, for generating input signals into the system 1 and in particular gearshifting requests, as well as an optional display device 30 with indicator lights like for example LEDs or with an alphanumeric display or with a graphical display—monochrome or colour—to provide visual information of the system 1 to the user. A rear or right manual control device 24, typically associated with the rear derailleur, a front or left manual control device 26 typically associated with the front derailleur and a manual control device 28 of the gear ratio are shown by way of an example.

Preferably, the interface 22 also allows the selection of options and/or the selection/input of values, for example embodying a suitable graphical interface with the controls 24, 26, 28 and the display 30, or providing for suitable keyboard or keypad.

Furthermore, in the interface 22 a sound emitting device, for example a beeper 31, can be provided for to provide feedback that can be heard by the cyclist.

The user interface 22 can be entirely absent—or it can comprise the output devices 30, 31 only—in the case in which only an automatic operating mode of the system 1 is provided for.

The system 1 can comprise one or more of the following sensors 32 of run-time variable quantities, which generate respective measurement or detection signals:
- a heart rate monitor 34, for detecting the heart rate of the cyclist, preferably provided with its own data memory 35 also used as buffer memory for storing data detected at a predetermined detection frequency and for transmitting to the controller 16 only upon request or at a sampling frequency that is lower than the detection frequency,
- a power sensor 36 that measures the power delivered by the cyclist, namely the product of the force applied to the pedals and the rotation cadence of the pedal cranks; this can for example be arranged at one of the following positions: crankset (assembly formed of the pedal cranks and the front toothed wheels), pedals, hub of the rear wheel or chain; moreover, the power sensor 36 can also be provided with its own data memory 37 also used as buffer memory for storing data detected at a predetermined detection frequency and for transmitting to the controller 16 only upon request or at a sampling frequency that is lower than the detection frequency,
- a cadence sensor 38 that measures the rotation cadence of the pedal cranks, typically in revolutions/minute (rpm); the cadence sensor 38 can also be provided with its own data memory 39 also used as buffer memory for storing data detected at a predetermined detection frequency and for transmitting to the controller 16 only upon request or at a sampling frequency that is lower than the detection frequency.

In particular, for the implementation of the Performance Index Training mode according to the invention described hereinafter, the system 1 comprises at least the heart rate monitor 34 and the power sensor 36.

Other sensors may also be provided for in the system 1.

The bicycle electronic system 1 can also comprise a cyclecomputer 40 associable even only temporarily with the system 1. Alternatively, the controller 16, the display 30, and the beeper 31 where provided for, as well as possible buttons of the interface 22, can consist of the components of the cyclecomputer 40.

Besides being suitably connected to the mechanical parts of the bicycle, the components of the system 1 lacking an internal power source are suitably connected—directly or indirectly—to the power source 18.

Moreover, the components of the system 1 are suitably in communication with the controller 16 and/or with each other. The communication can be wireless, wired, or hybrid.

The wired communication preferably takes place with a serial protocol. The wired communication can take place with point to point connections or through a communication bus.

The wireless communication takes place for example according to one of the low energy consumption communication protocols ZigBee, ANT+ or BTLE (BlueTooth Low Energy).

The system 1 can therefore comprise one or more wireless-to-wired and/or wired-to-wireless transducers 42.

In particular, the heart rate monitor 34 is preferably of the wireless type so as not to hamper the movements of the cyclist and a transducer 42 is arranged between the heart rate monitor 34 and the controller 16.

The connection of the various components of the system 1 in a network, and in particular in a wireless network, allows several functionalities. Just by way of an example, on the display device 30 it is possible to display information relating to the remaining autonomy of the battery in terms of time.

In a per se known way, the communication network among the components of the system 1 can be established and/or configured, for example through a portable computer (PC) with a wireless key and ad hoc application, preferably with wireless connection. In a per se well known way, the configuration can take place on the basis of the "MAC addresses" of the devices of the system 1. In the case of a wireless network, at the moment of establishing the network, replacing a node or adding a node, a recognition and mutual acceptance procedure is used, so that only the addresses forming part of the created group are accepted within the network, and those external thereto are ignored, being recognised as disturbances.

The procedure for creating the network requires the exchange of a series of data packets with a numerical key variable according to a predetermined law for enabling the programming of the network (creation of the group) and subsequent confirmation.

As schematised in FIG. 2 and in FIG. 3, the controller 16 of the system 1 and the method for actuating the gearshift according to the invention, respectively, can implement at least one of:
- an automatic control 60 of a "biomechanical system" 62 to be controlled, consisting of the bicycle and the cyclist 64, in particular consisting of the gear ratio engaged in the gearshift 10 of the bicycle and the heart rate of the cyclist 64 and/or the power transmitted by the cyclist 64 to the bicycle, and
- a semi-automatic control 68 of the "biomechanical system" 62;
- they can also advantageously implement
- a manual control 66 of the gearshift 10.

In the system 1 there are means 70 for selecting the type of control among the controls 60, 66, 68. The selection means 70 in FIG. 2 are depicted purely diagrammatically by a rhombus, as other selection means described hereinafter and depicted in the other figures.

The selection means 70, as other selection means described hereinafter and depicted in the other figures, can comprise manual selection means by the user and/or automatic selection means by the controller 16 itself.

The type of control currently active is preferably suitably stored in the memory 17.

As schematised in FIG. 3, the automatic control 60 is of the closed loop type.

The controlled variable(s) is/are selected from:
the heart rate of the cyclist,
the pedalling power,
a performance index given preferably by the ratio between the pedalling power and the heart rate:

$$\text{performance index} = \text{power}/\text{heart rate} \quad (1)$$

The possible detected variables 72 or measured outputs are therefore:
detected_heart_rate emitted by the heart rate monitor 34,
detected_power emitted by the power sensor 36,
detected_performance_index=detected_power/detected_heart_rate, calculated by the controller 16 itself.

The possible reference or desired variables 74 are therefore:
heart_rate_setpoint,
power_setpoint,
performance_index_setpoint
and they are generically indicated as setpoint 74. With the ordinary meaning, under the term "setpoint" the desired output of the biomechanical system 62 that the automatic control wishes to reach is meant.

It should be emphasized that a performance index that links the pedalling power and the heart rate, and in particular that given by formula (1), is not known in the field, and the automatic control of the gearshift 10 based on such a performance index represents an inventive aspect per se, even independently of other aspects described herein.

The control variable is the gear ratio of the gearshift 10, gear ratio. The gear ratio is controlled through a signal 76 generated by the controller 16 for the gearshift 10, indicated as control signal.

As described in detail hereinafter, the controller 16, and in particular a module 78 thereof, generates the signal 76 control_signal based on the difference between at least one of the detected variables 72 and the corresponding reference variable 74, a difference which is also indicated as error 80.

The controller 16 and in particular its module 78 can receive in input, besides the error 80, also the output of the various sensors 32 of the system and in particular the output of the power sensor 36 and/or of the heart rate monitor 34 and/or of the cadence sensor 38.

FIG. 4 is a functional block diagram that illustrates the exchange among the main components of the system 1 of the values of the main parameters, variables and/or quantities that intervene in the method for actuating the gearshift of the invention.

The controller 16 can receive in input one or more of the following quantities:
(a) the quantity detected_heart_rate from the heart rate monitor 34,
(b) the quantity detected_power from the power sensor 36,
(c) the quantity detected_cadence from the cadence sensor 38,
(d) the signal gearshifting_request from the user interface 22,
(e) the setpoint from the user interface 22 (heart_rate_setpoint and/or power_setpoint and/or performance_index_setpoint),
(f) the desired training mode and other selections,
(g) the current gear ratio from the gearshift 10, gear_ratio;

the controller 16 can emit one or more of the following quantities:
(h) a suitable feedback to the user interface 22,
(i) the control signal to the gearshift 10, control_signal.

As far as the element (d) indicated above is concerned, the signal gearshifting_request can, in the gearshifts of the second type discussed above, be a signal requesting an increase in the gear ratio increase_ratio_request or a signal requesting a reduction in the gear ratio decrease_ratio_request, or, in gearshifts of the first type discussed above, a signal requesting movement in a specific direction of a specific derailleur between the rear derailleur 12 and the front derailleur 14. For the sake of simplicity reference shall be made hereinafter only to the requests increase_ratio_request and decrease_ratio_request suitable for gearshifts of the second type discussed above, the changes to be made in the case of gearshifts of the first type discussed above being within the capabilities of one skilled in the art in light of the present description.

As far as the element (e) is concerned, the setpoint can be of various types, as stated above. The user interface 22 can be used to select which of the three (or more) setpoints to use. Moreover, the user interface 22 can be used to directly input the value of the preselected setpoint, namely the value of the quantity(ies) heart_rate_setpoint, power_setpoint, performance_index_setpoint, or the related value can be a default value stored in the memory 17 in the factory and/or a value previously stored by the user in the memory 17 in a setting mode of the system 1.

Relative to the element (g) it is worth emphasizing that there are many modes of representation within the system 1 of the gear ratio of the gearshift 10, and the present invention is not restricted to any specific mode. For example, it is possible to numerically indicate the actual gear ratio, indicated as the number of revolutions of the pedal cranks for each revolution of the rear wheel; it is also possible to indicate the number of teeth of the toothed wheel with which the chain is currently engaged (with two separate indications for the front group of toothed wheels and the rear group of toothed wheels); or the toothed wheel number in a numbering for example of the smallest to the largest (with two separate indications for the front group of toothed wheels and the rear group of toothed wheels).

Similarly, the control signal (i) sent to the gearshift 10 by the controller 16 can be susceptible of various representations within the system 1, for example according to the mode of representation of the gear ratio and/or of the type of electromechanical actuator, and the specific mode lies outside the present invention.

As stated, for the sake of simplicity, in the rest of the present description reference will be made to generic signals increase_ratio and decrease_ratio. For example, a signal increase_ratio could be equivalent to a command to pass to a toothed wheel with a smaller diameter and/or smaller number of teeth among those associated with the hub of the rear wheel, and/or to a command to pass to a toothed wheel with a greater diameter and/or greater number of teeth among those associated with the axle of the pedal cranks. Moreover, such a command could be equivalent to a command to actuate the electric motor of the derailleur for a certain time or at a given voltage, or to a different command suitable for the electromechanical parts of the system 1.

Finally, the feedback to the user interface 22 indicated at (h) can be in any form that is intelligible to the cyclist, including alphanumeric characters, graphics, sounds, and it can concern the setpoint 74, and/or the output of the sensors 32 and/or the status of the system 1 and in particular of the gearshift 10 and/or the status of the cyclist himself.

Returning to FIG. 2, in the automatic control mode 60 the controller 16 evaluates the conditions of the biomechanical system 62 as will be described in detail hereinafter, and the manual control devices 24, 26, 28 are absent, are not network-connected, or the commands output by them are totally ignored by the controller 1.

In the manual control mode 66, the cyclist inputs the gearshifting requests that he deems appropriate through the electromechanical manual control device(s) 24, 26, 28, at the time he/she deems appropriate. Such device(s) 24, 26, 28 output(s) the signal gearshifting_request—in particular, increase_ratio_request or decrease_ratio_request—for the gearshift 10, which actuates such gearshiftings. More specifically, the signal gearshifting_request can be received by the controller 16 that, having possibly carried out some checks—for example that the gearshift is not already at the maximum gear ratio when it receives the signal increase_ratio_request—outputs a suitable signal for the gearshift 10, again indicated herein as control_signal—in particular increase_ratio or decrease_ratio. The sensors 32 are absent, are not network-connected, or the measurement values output by them are totally ignored by the controller 1.

Also in the semi-automatic control mode 68, the cyclist inputs the gearshifting requests that he deems appropriate through the electromechanical manual control device(s) 24, 26, 28, at the time he/she deems appropriate. Such device(s) 24, 26, 28 output(s) the signal gearshifting request—in particular, increase_ratio_request or decrease_ratio_request—and the controller 16 receives it. Independently thereof and in parallel therewith, the automatic control module 60 evaluates the conditions of the biomechanical system 62 as will be described relative to the automatic control 60 itself, and establishes when it is suitable to send a control_signal control_signal—in particular increase_ratio or decrease_ratio. The controller 16 manages the conflicts between the requests of the cyclist and the requests generated internally differently according to a mode that preferably can be selected of semi-automatic control with manual priority 82 and semi-automatic control with automatic priority 84, wherein means 86 are provided for to select between these two modes.

Preferably and unlike what is known from U.S. Pat. No. 6,047,230, the default mode is semi-automatic control with automatic priority 84. In semi-automatic control with automatic priority 84, the controller 16 monitors the output of the heart rate monitor 34 and/or that of the power sensor 36; so long as the monitored output is present and is updated with a predetermined minimum periodicity, indicative of the fact that the heart rate monitor 34 and/or the power sensor 36 are operating correctly, the controller 16 disables the manual commands. Especially in the case of at least partially wireless communication within the system 1, the manual control devices 24, 26, 28 of the user interface 22 are preferably inhibited also from transmitting the commands received from the cyclist into the rest of the system 1. In practice, each manual control device 24, 26, 28 comprises a processor part of the controller 16 with which it implements for example an enabling/disabling flag, and ignores the commands of the cyclist in the case of disabling, without forwarding them into the rest of the system 1. As soon as a problem is encountered relative to the heart rate monitor 34 and/or to the power sensor 36, or the absence of the heart rate monitor 34 and/or of the power sensor 36, and/or the absence of communication network, the controller 16 enables the manual controls and the system enters into the manual control mode 66.

This provision, which advantageously allows network traffic to be spared, the risk of errors and interference to be minimized, the possible internal batteries of the manual control devices 24, 26, 28 to be preserved, the performance of the semi-automatic control 68 to be made more fluent, is an inventive aspect in itself, also independently of other aspects described herein.

In the semi-automatic control with manual priority 82, the controller 16 on the other hand carries out each gearshifting requested by the cyclist (except, as stated above, when the gearshift is already in an extreme position) and, upon receiving such a gearshifting request, temporarily disables the automatic control. For example, when he/she sees a climb or a descent ahead, in this mode the cyclist can decide in advance of the controller 16 that it is suitable to change gear ratio.

Preferably, when plural sampling times of the output of the sensors 32 are provided for, as described hereinafter with reference to FIG. 8, the temporary disabling is for the longest sampling time.

In the semi-automatic control with manual priority 82, as an alternative or in addition to the aforementioned temporary priority of manual gearshifting requests over the gearshifting requests generated by the controller 16, the controller 16 can all the time perform the automatic control 60 in background, but transmit the auto-generated gearshifting requests to the gearshift 10 only when the conditions of the biomechanical system 62 become critical for the safety of the cyclist and/or for the mechanical soundness of the gearshift 10. In practice, this can be made possible, for example, with checks that the variables detected_heart_rate and/or detected_power and/or detected_performance_index remain within a predetermined range of values, namely that they do not exceed an upper threshold and/or they do not fall below a lower threshold.

Such a control of critical conditions can also be carried out in the case of manual control 66.

When the bicycle is motionless, the system 1 and in particular its controller 16 can be in an OFF state in which it is disconnected from the power source 18. Moreover, the system 1 and in particular its controller 16 can have a SLEEP state in which they operate in low power consumption mode, for example when they are awaiting commands from the user.

The automatic control 60—as stated above, also carried out in the semi-automatic control mode 68 in parallel to the monitoring of the manual commands input through the manual control devices 24, 26, 28—provides for different modes according to the type of training that the cyclist wishes to perform.

Irrespective of the preselected training mode, the controller 16 preferably carries out an initial Warm-up mode or step that is described hereinafter with reference to FIG. 15.

Alternatively or in addition thereto, irrespective of the preselected training mode, at the end thereof the controller 16 preferably carries out a Cool-down mode or step which is described hereafter with reference to FIG. 16.

The training modes can include one or more of the modes illustrated in FIG. 5 and better described hereinafter, which correspond above all to the controlled variable(s) indicated above: Heart Rate Training 120, Power Training 122, and Performance Index Training 124. Means 126 for selecting the training mode are provided for.

The controller 16 monitors the outputs of the sensors 32 and possibly takes the following actions:

if Heart Rate Training 120 has been selected, but the controller 16 does not receive the output of the heart rate monitor 34—because the device is absent or turned off or because there are communication problems—then the controller 16 sets the manual control type 66;

if Power Training 122 has been selected, but the controller 16 does not receive the output of the power sensor 36—because the device is absent or turned off or because there are communication problems—then the controller 16 sets the manual control type 66;

if Performance Index Training 124 has been selected, but the controller 16 does not receive the output of the heart rate monitor 34 and/or that of the power sensor 36, then the controller 16 sets the manual control type 66.

In turn, the Heart Rate Training mode 120 can preferably be selected among the following modes, not all necessarily available:

Basic Zone 128, wherein a relatively low predetermined heart rate is set as reference variable 74, Intensive Zone 130, wherein a medium predetermined heart rate is set as reference variable 74, Maximal Zone 132, wherein a relatively high predetermined heart rate is set as reference variable 74, Customized 134, wherein a heart rate freely selected by the user (possibly subject to the check that it falls within a predetermined range of values) is set as reference variable 74.

Means 136 for selecting among the aforementioned training modes are provided for.

In an alternative embodiment, each of such Zone modes is associated with a respective predetermined time period basic_zone_time, intensive_zone_time, maximal_zone_time, and the controller 16 carries out cyclical switching among the three Zone modes, carrying out each mode for the respective predetermined time period, as schematised by the arrows 137a, 137b, 137c.

A suitable value for the predetermined heart rate in the aforementioned three Zone modes ranges in three ranges ranging overall from 35 to 300 bpm. Preferably each predetermined heart rate is a variable the value of which is stored in the memory 17. Preferably, such a value can be modified by the user.

A suitable value for the predetermined time period basic_zone_time, intensive_zone_time, maximal_zone_time representative of the duration of each of the aforementioned three Zone modes preferably ranges from 0 to 200 minutes. Preferably each duration is a variable the value of which is stored in the memory 17. Preferably, such a value can be modified by the user.

A suitable value for the heart rate freely selectable by the user ranges from 35 to 300 bpm. Preferably, such a freely selectable heart rate is a variable the value of which is stored in the memory 17. Preferably, such a value can be modified by the user.

In each of such Heart Rate Training modes 120, the reference variable 74 is therefore the heart rate indicated as heart_rate_setpoint, as schematized in block 138.

The Power Training mode 122 can preferably be selected among the following modes:

Simple 140, wherein a constant predetermined pedalling power is set as reference variable 74, With Repetitions 142, wherein a pedalling power that is variable according to a stepped progression, better described hereinafter, is set as reference variable 74.

Means 144 for selecting among the aforementioned Power Training modes are provided for.

In each of such Power Training modes 122, the reference variable 74 is therefore the pedalling power indicated as power_setpoint, as schematized in block 146.

In the Performance Index Training mode 124, the reference variable 74 is the performance index preferably given by the formula (1), indicated as performance_index_setpoint, as schematized in block 148.

A suitable value for the reference performance index ranges from 0.5 to 10 watt/bpm. Preferably, such a performance index is a variable the value of which is stored in the memory 17. Preferably, such a value can be modified by the user.

It should however be understood that the means or modules for selecting the training mode 126, 136, 144 can be combined, so that the selection does not necessarily have to take place on two levels.

As stated, in the Repetitions Training mode 142 the reference variable 74 is a predetermined pedalling power that is variable according to a stepped progression. With reference to FIG. 6, the predetermined pedalling power preferably takes up four constant values, each for a respective predetermined time period, and the sequence preferably repeats cyclically. Thus, the predetermined pedalling power takes up the value P_recovery for the time period recovery_time, the value P_threshold_1 for the time period threshold_1_time, the value_P_threshold_2 for the time period threshold_2_time, the value P_max for the time period P_max_time, and then from the beginning.

A suitable value for the predetermined pedalling power at the aforementioned four constant values P_recovery, P_threshold_1, P_threshold_2, P_max ranges in four ranges extending overall from 0 to 3,000 watt. Preferably, each constant predetermined pedalling power value is a variable the value of which is stored in the memory 17. Preferably, such a value can be modified by the user.

A suitable value for each of the aforementioned time periods recovery_time, threshold_1_time, threshold_2_time, P_max_time ranges from 0 to 200 minutes. Preferably, each of the aforementioned values is a variable the value of which is stored in the memory 17. Preferably, such a value can be modified by the user.

It is possible to provide for less than four or more than four power steps.

Moreover, it is not necessary for the power to vary according to an increasing stepped progression and then for such a progression to repeat: it is possible to provide for a progression that first increases and then decreases, and other variants.

It should be emphasized that the provision of an automatic control of the gear ratio based on the pedalling power with cyclical variation of the reference value, as the Repetition Training 142, is deemed to be an aspect that is inventive in itself, independently of other aspects described herein.

FIG. 7 illustrates an embodiment of a flow chart relating to the method for actuating the gearshift according to the invention, at a level independent of the preselected training type.

First of all a block 150 of acquisition of the setpoint 74 set in blocks 138, 146, 148 of FIG. 5, and a block 152 of acquisition of the duration of a time period indicated as sampling_time, better described hereinafter, are illustrated. These two operations or steps are not necessarily sequential and can be carried out at any time before a particular training, or even one-off (una tantum) or occasionally by a cyclist. In the case of Repetition Training, the block 150 of acquisition of the setpoint 74 is carried out plural times during a training, as stated above.

In a block 154, a timer is triggered that monitors the elapsing of the time period sampling_time.

In a block 156 it is checked whether the time period sampling_time has elapsed (timer run out), remaining in such a block until such a time period has elapsed.

In a block 158 the controller 16 evaluates the current conditions of the biomechanical system 62, in particular the detected variables 72, with respect to the setpoint 74 acquired in block 150.

In a block 160, the controller 16 establishes, based on such evaluation, whether it is necessary to change the gear ratio of the gearshift 10.

In the negative case, the gearshift 10 is not moved and block 154 is returned to wait a further time period sampling_time.

In the positive case, the controller 16 checks in a block 162 the presence of alarm conditions, and in particular whether the heart rate detected by the heart rate monitor 34, detected_heart_rate, is above a predetermined heart rate threshold corresponding to the "anaerobic threshold", indicated herein as anaerobic_threshold. The "anaerobic threshold" is an indicator used in sports medicine and is per se well known, even though it has no unequivocal definition. For the purposes of the present invention it is however irrelevant how the anaerobic threshold is calculated. In block 162 it is therefore checked whether:

$$\text{detected\_heart\_rate} > \text{anaerobic\_threshold?} \tag{2}$$

A suitable value for the heart rate threshold anaerobic_threshold is equal to or greater than 170 bpm (beats per minute). Preferably, such a threshold is a variable the value of which is stored in the memory 17. Preferably, such a value can be modified by the user.

If the check of block 162 has given a negative outcome, in a block 164 the controller outputs the control signal for the gearshift 10 control_signal.

If the check of block 162 has given a positive outcome, in a block 166 the system 1 switches to an ALARM state.

In the ALARM state 166, the controller 16 decreases the gear ratio of the gearshift 10 to allow the heart rate of the cyclist to be lowered, since less effort is required, and to prevent acidosis taking the cyclist into critical situation for performance.

Preferably, the gearshift 10 is kept in the new gear ratio condition for a predetermined time period, indicated herein as alarm_timeout.

A suitable value for the predetermined time period alarm_timeout ranges from 0 to 100 minutes. Preferably, such a predetermined time period is a variable the value of which is stored in the memory 17. Preferably, such a value can be modified by the user.

In a way that is not shown, the controller 16 can check whether the heart rate detected by the heart rate monitor 34, detected_heart_rate, stays above the anaerobic_threshold for a predetermined time period, indicated as SA_timeout, and enter into the ALARM state 166 only in this case, therefore allowing short heart rate spikes.

In an alternative that is not shown in general, but shown in the detailed diagrams described later on, the check of the alarm conditions is carried out only if in block 160 the controller 16 determines that it has to reduce the gear ratio, and thus before outputting the signal 76 decrease_ratio, while the signal increase_ratio is immediately output.

It should be emphasized that the provision of an alarm threshold based on the anaerobic threshold in combination with an automatic control of the gear ratio based on the output of one or more of the sensors 32 and in particular based on pedalling power and/or on heart rate, is deemed to be an aspect that is inventive in itself, independently of other aspects described herein.

As stated, the heart rate monitor 34, the power sensor 36 and/or the cadence sensor 38 is/are preferably provided with its/their own data memory 35, 37, 39 also used as buffer memory for storing the data detected at a predetermined detecting frequency and for transmitting to the controller 16 only upon request or at a sampling frequency—the inverse of the sampling time acquired in block 154—lower than the detection frequency.

Preferably, the detection frequency is preset by the manufacturer of the heart rate monitor 34, of the power sensor 36 and/or of the cadence sensor 38.

With reference to FIG. 8, preferably the system 1 provides that the time period indicated as sampling_time, namely the sampling frequency referred to in blocks 152, 154, 156 of FIG. 7, is selectable, through selection means 170, from at least two different possibilities, preferably among four different possibilities.

Preferably there are provided for:
- a relatively low sampling frequency, with which a relatively long sampling time period is associated; preferably this sampling frequency is used in the Basic Zone Training mode 128; the value of the parameter sampling_time, relatively high, is indicated as slow_time 172;
- a medium sampling frequency, with which a medium sampling time period is associated; preferably this sampling frequency is used in the Intensive Zone Training mode 130; the value of the parameter sampling_time, relatively medium, is indicated as medium_time 174;
- a relatively high sampling frequency, with which a relatively short sampling time period is associated; preferably this sampling frequency is used in the Maximal Zone Training mode 132; the value of the parameter sampling_time, relatively low, is indicated as fast_time 176;
- an automatic sampling frequency, with which an automatically variable sampling time period is associated, preferably as a function of the heart rate detected by the heart rate monitor 34, more preferably with an inversely variable relationship: as the detected heart rate increases, the sampling frequency increases; the value of the parameter sampling_time is indicated as automatic_time 178.

In the Customized Training mode 134, the sampling frequency is preferably selected as automatic.

In the Power Training mode 122, the sampling frequency is preferably selected as the relatively high one (fast_time 176).

In the Performance Index Training mode 124, the sampling frequency is preferably selected as the automatic one.

A suitable value for each of the aforementioned time periods slow_time, medium_time, fast_time ranges in three ranges ranging overall from 0.2 to 10 seconds. Preferably, each of the aforementioned values is a variable the value of which is stored in the memory 17. Preferably, such a value can be modified by the user.

A suitable value for the aforementioned time period automatic_time ranges from 0.2 to 10 seconds. Preferably, the aforementioned value is a variable the value of which is stored in the memory 17. Preferably, such a value can be modified by the user.

By providing for more than one sampling frequency and therefore an evaluation of the parameters of the biomechanical system 62 that is more or less frequent, it is possible, in automatic control 60, to better pursue the setpoint 74 set, and therefore it is possible to get there earlier and allow only smaller offsets from such a setpoint 74. Moreover, providing for more than one sampling frequency allows for example the network traffic in the system 1 to be reduced when the heart rate—or other control variable—is changing slowly, and thus to optimize the pass band of the communication network established within the system 1.

It should be emphasized that providing for more than one sampling frequency represents an inventive aspect per se, even independently of other aspects described herein.

Figure 9:
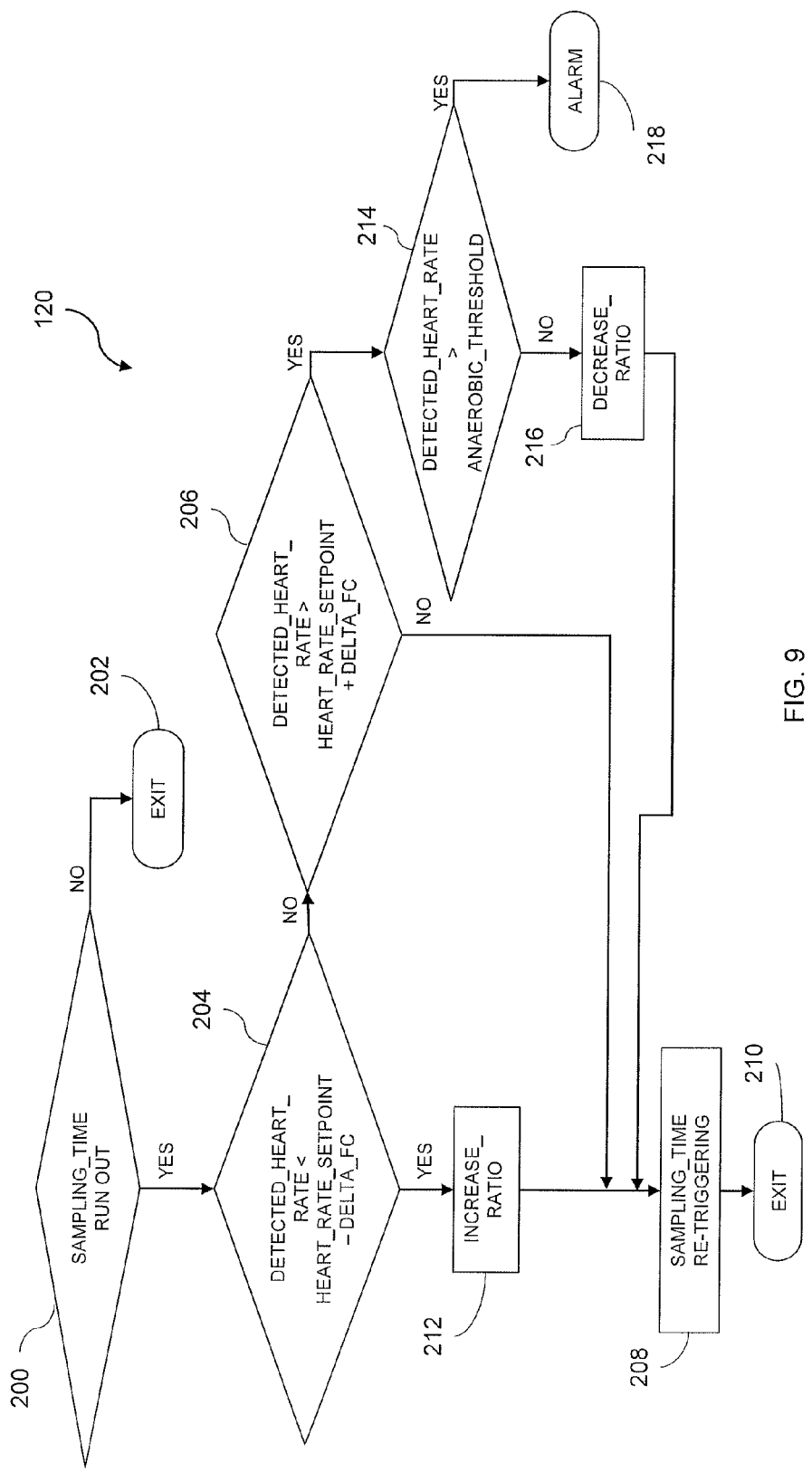

FIG. 9 illustrates a more detailed flow chart relating to a cycle of the Heart Rate Training 120, irrespective of the preselected sub-mode Basic Zone 128, Intensive Zone 130, Maximal Zone 132 or Customized 134.

This cycle—as will be seen—repeats at the sampling frequency preselected as described with reference to FIG. 8, except the case of entry into ALARM state. In other words, the value of the variable sampling_time is that which was set as described with reference to FIG. 8.

In a block 200 it is checked whether the sampling time period sampling_time has elapsed, as indicated by the running out of a timer that had previously been triggered when the training started.

If the sampling time has not elapsed, the cycle ends in an exit block 202, to start again from block 200.

If, on the other hand, the sampling_time has elapsed, in blocks 204, 206 it is checked whether the detected_heart_rate is in a predetermined "reference area", for example of width 2*Delta_Fc, about the set reference value heart_rate_setpoint, respectively checking the conditions:

$$\text{detected\_heart\_rate} < \text{heart\_rate\_setpoint} - \text{Delta}\_Fc \quad (3)$$

$$\text{detected\_heart\_rate} > \text{heart\_rate\_setpoint} + \text{Delta}\_Fc \quad (4)$$

The "reference area" can for example be of a size comparable to the resolution of the heart rate monitor 34. In this way, the system 1 ignores very small differences, which could result in too frequent gearshifting. For example Delta_Fc can be 1 bpm.

The "reference area" does not necessarily have to be symmetrical about the set reference value heart_rate_setpoint, namely the values subtracted and added in the formulae (3) and (4) do not necessarily have to be equal to each other.

In the case in which both of the blocks 204, 206 have a negative outcome, the timer relative to the sampling_time period sampling_time is re-triggered in a block 208 and the cycle ends, in a block 210.

In the case in which the block 204 has a positive outcome, and therefore the detected heart rate is less than the lower limit of the reference area in that the check of formula (3) has given a positive outcome, in a block 212 the automatic control 60 acts to increase the effort of the cyclist 64 by increasing the gear ratio. The controller 16 thus outputs the command increase_ratio. It should be noted as of now that in this step, as in analogous steps of outputting the command increase_ratio or the command decrease_ratio described with reference to this FIG. 9 and to the subsequent FIGS. 10-12, the gear ratio can be modified in various ways, better described hereinafter with reference to FIGS. 13-14.

Once the control signal or command increase_ratio has been output, or once such a command has been actuated in the gearshift 10, the timer relative to the sampling time period sampling_time is re-triggered in block 208 and the cycle ends, in block 210.

In the case in which the check of block 206 gives a positive outcome, and therefore the detected heart rate is above the upper limit of the reference area in that the check of the formula (4) has given a positive outcome, the controller 16 must act to decrease the effort of the cyclist 64, by decreasing the gear ratio.

Preferably, if the relative option is enabled, before proceeding to output the related command decrease_ratio, the controller checks, in a block 214, whether the detected heart rate is above the anaerobic threshold value, formula (2) above.

In the negative case, in a block 216 the controller 16 outputs the command decrease_ratio and proceeds with block 208 of re-triggering the timer relative to the sampling time period sampling_time, and with block 210 of exit block 210 from the procedure.

In the positive case, on the other hand, in a block 218 the ALARM state described above with reference to block 166 of FIG. 7 is entered. As stated there, the ALARM state can be activated when the formula (2) is satisfied for a predetermined minimum time period, so as to tolerate brief heart rate spikes.

Summarising, in the Heart Rate Training mode, the heart rate of the cyclist is brought to the desired heart rate through adjustment of the gear ratio, and it is not allowed to exceed the anaerobic threshold (except possibly for a sufficiently short time period).

Figure 10:
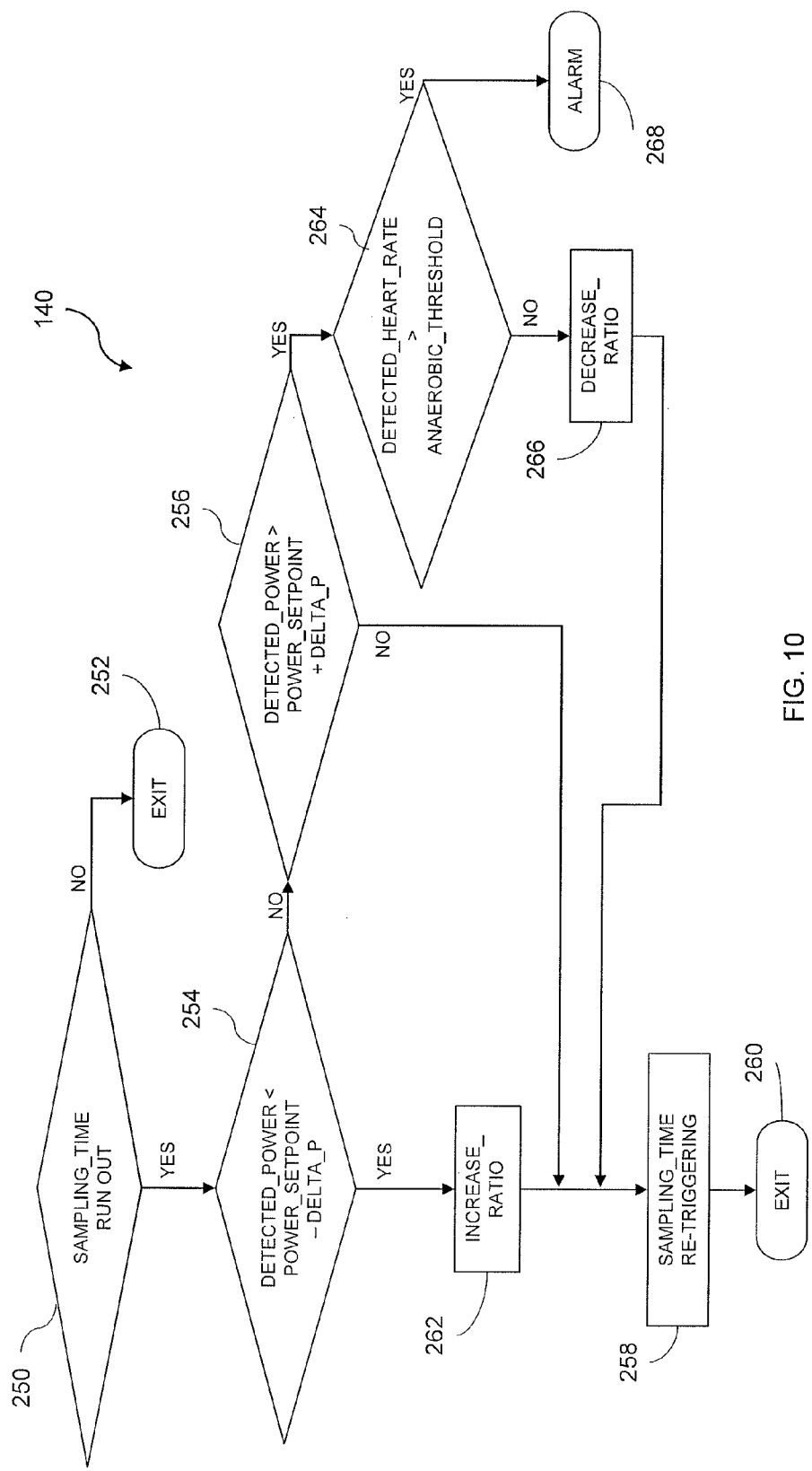

FIG. 10 illustrates a more detailed flow chart relative to the cycle of Simple Power Training 140.

This cycle—as shall be seen—repeats at the sampling frequency preselected as described with reference to FIG. 8, except for the case of entry into ALARM state.

In a block 250 it is checked whether the sampling time period sampling_time has elapsed, as indicated by the running out of a timer that had previously been triggered when training started.

If the sampling_time has not elapsed, the cycle ends in an exit block 252, to start again from block 250.

If, on the other hand, the sampling_time has elapsed, in blocks 254, 256 it is checked whether the power detected is in a predetermined "reference area", for example of width 2*delta_P, about the set reference value power_setpoint, respectively checking the conditions:

$$\text{detected\_power} < \text{power\_setpoint} - \text{Delta}\_P \quad (5)$$

$$\text{detected\_power} > \text{power\_setpoint} + \text{Delta}\_P \quad (6)$$

The "reference area" can for example be of a size comparable to the resolution of the power sensor 36. In this way, the system 1 ignores very small differences, which could result in too frequent gearshifting. For example Delta_P can be 20 watt.

The "reference area" does not necessarily have to be symmetrical about the set reference value power_setpoint, namely the values subtracted and added in the formulae (5) and (6) do not necessarily have to the equal to each other.

In the case in which both of the blocks 254, 256 have a negative outcome, the timer relative to the sampling time period sampling_time is re-triggered in a block 258 and the cycle ends, in a block 260.

In the case in which the block 254 has a positive outcome and therefore the detected power is below the lower limit of the reference area in that the check of formula (5) has given a positive outcome, in a block 262 the automatic control 60 acts to increase the effort of the cyclist 64 and decrease the pedalling cadence by increasing the gear ratio. The controller 16 thus outputs the command increase_ratio.

Once the control signal or command increase_ratio has been output, or once such a command has been actuated in the gearshift 10, the timer relative to the sampling time period sampling_time is re-triggered in block 258 and the cycle ends, in block 260.

In the case in which the check of block 256 gives a positive outcome, and therefore the detected power is above the upper limit of the reference area in that the check of formula (6) has given a positive outcome, the controller 16 must act to decrease the effort of the cyclist 64 and increase the pedalling cadence, by decreasing the gear ratio.

Preferably, if the relative option is enabled, before proceeding to output the related command decrease_ratio, the controller checks, in a block 264, whether the detected heart rate is above the anaerobic threshold value, formula (2) above.

In the negative case, in a block 266 the controller 16 outputs the command decrease_ratio and proceeds with block 258 of re-triggering the sampling time period sampling_time, and with block 260 of exit block 260 from the procedure.

In the positive case, on the other hand, in a block 268 the ALARM state described above with reference to block 166 of FIG. 7 is entered. As stated there, the ALARM state can be activated when the formula (2) is satisfied for a predetermined minimum time period, so as to tolerate brief heart rate spikes.

Summarising, in the Power Training mode, the pedalling power is brought to the desired power through adjustment of the gear ratio, and the heart rate is not allowed to exceed the anaerobic threshold (except possibly for a sufficiently short time period).

FIG. 11 illustrates a more detailed flow chart relative to the Repetitions Training cycle 142.

This cycle differs from that of Power Training 140 just described with reference to FIG. 10 in that, as already described with reference to FIG. 6, the power setpoint is in this case variable according to a stepped progression.

This cycle—as shall be seen—repeats at the sampling frequency preselected as described with reference to FIG. 8, except for the case of entry into ALARM state.

In a block 300 it is checked whether the sampling time period sampling_time has elapsed, as indicated by the running out of a timer that had previously been triggered when training started.

If the sampling time has not elapsed, the cycle ends in an exit block 302, to start again from block 300.

If, on the other hand, the sampling time has elapsed, in a block 304 it is checked, with reference to a timer relative to the variable Pmax_time that was initially triggered at the start of the training, whether it is in the maximum power step of the desired stepped progression. In the affirmative case, in a block 306 the reference value power_setpoint is set at the value of the variable P_max.

In the negative case, in a block 308 it is checked, with reference to a timer relative to the variable threshold_2_time that was initially triggered at the start of training, whether it is in the power step relative to the step below that of maximum power. In the affirmative case, in a block 310 the reference value power_setpoint is set at the value of the variable P_threshold_2.

In the negative case, in a block 312 it is checked, with reference to a timer relative to the variable threshold_1_time that was initially triggered at the start of training, whether it is in the power step relative to the step below. In the affirmative case, in a block 314 the reference value power_setpoint is set at the value of the variable P_threshold_1.

In the negative case, in a block 316 it is checked—even though redundantly, since the blocks 304, 308, 312, 316 are actually a "CASE" instruction—, with reference to a timer relative to the variable recovery_time that was initially triggered at the start of training, whether it is in the power step relative to the lowest step. In the affirmative case, in a block 318 the reference value power_setpoint is set at the value of the variable P_recovery.

The checks outlined above of the blocks 304, 308, 312, 316 can take place in a different order from what has been shown.

In any of the four cases, in blocks 320, 322 it is checked whether the detected power is in a predetermined "reference area", for example of width 2*delta_P, about the set reference value power_setpoint, checking (like in the case of FIG. 10) the conditions given by the formulae (5) and (6), respectively.

The "reference area" can for example be of a size comparable to the resolution of the power sensor 36. In this way, the system 1 ignores very small differences, which could result in too frequent gearshifting. For example delta_fc can be 20 watt.

The "reference area" does not necessarily have to be symmetrical about the set reference value power_setpoint, namely the values subtracted and added in the formulae (5) and (6) do not necessarily have to be equal to each other.

In the case in which both of the blocks 320, 322 have a negative outcome, the timer relative to the time period of the current step recovery_time, threshold_1_time, threshold_2_time, Pmax_time, is re-triggered in a block 324, the timer relative to the sampling time period sampling_time is re-triggered in a block 326, and the cycle ends, in a block 328.

In the case in which the block 320 has a positive outcome and therefore the detected power is below the lower limit of the reference area in that the check of the formula (5) has given a positive outcome, in a block 330 the automatic control 60 acts to increase the effort of the cyclist 64 with a slight decrease in the pedalling cadence, by increasing the gear ratio. The controller 16 thus outputs the command increase_ratio.

Once the control signal or command increase_ratio has been output, or once such a command has been actuated in the gearshift 10, in block 324 the timer relative to the time period of the current step recovery_time, threshold_1_time, threshold_2_time, Pmax_time, is re-triggered.

Moreover, the timer relative to the sampling_time period sampling_time is re-triggered in block 326 and the cycle ends, in a block 328.

In the case in which the check of block 322 gives a positive outcome, and therefore the detected_power is above the upper limit of the reference area in that the check of the formula (6) has given a positive outcome, the controller 16 must act to decrease the effort of the cyclist 64 and increase the pedalling cadence, by decreasing the gear ratio.

Preferably, if the relative option is enabled, before proceeding to output the related command decrease_ratio, the controller checks, in a block 332, whether the detected heart rate is above the anaerobic threshold value, formula (2) above.

In the negative case, in a block 334 the controller 16 outputs the command decrease_ratio and proceeds with block 324 of re-triggering the time period of the current step recovery_time, threshold_1_time, threshold_2_time, Pmax_ time, with block 326 of re-triggering the sampling time period sampling_time, and with the block 328 of exit from the procedure.

In the positive case, on the other hand, in a block 336 the ALARM state described above with reference to block 166 of FIG. 7 is entered. As stated there, the ALARM state can be activated when formula (2) is satisfied for a predetermined minimum time period, so as to tolerate brief heart rate spikes.

Summarising, also in the Repetitions Training mode, the pedalling power is brought to the power desired on each occasion in the stepped progression according to FIG. 6 through adjustment of the gear ratio, and the heart rate is not allowed to exceed the anaerobic threshold (except possibly for a sufficiently short time period).

FIG. 12 illustrates a more detailed flow chart relative to the cycle of Performance Index Training 124.

This cycle—as will be seen—repeats at the sampling frequency preselected as described with reference to FIG. 8, except for the case of entry into ALARM state.

In a block 350 it is checked whether the sampling time period sampling_time has elapsed as indicated by the running out of a timer that had previously been triggered when training started.

If the sampling_time has not elapsed, the cycle ends in an exit block 352, to start again from block 350.

If, on the other hand, the sampling time has elapsed, in blocks 354, 356 it is checked whether the detected performance index is in a predetermined "reference area", for example of width 2*k, about the set reference value performance_index_setpoint, respectively checking the conditions:

$$\text{detected\_performance\_index} < \text{performance\_index\_setpoint} - k \quad (7)$$

$$\text{detected\_performance\_index} > \text{performance\_index\_setpoint} + k \quad (8)$$

The "reference area" can for example be of a comparable size to the resolution of the heart rate monitor 34 and/or of the power sensor 36. In this way, the system 1 ignores very small differences, which could result in too frequent gearshifting. For example k can be 0.05 W/bpm.

The "reference area" does not necessarily have to be symmetrical about the set reference value performance_index_setpoint, namely the values subtracted and added in the formulae (7) and (8) do not necessarily have to be equal to each other.

In the case in which both of the blocks 354, 356 have a negative outcome, the timer relative to the sampling_time period sampling_time is re-triggered in a block 358 and the cycle ends, in a block 360.

In the case in which the block 354 has a positive outcome and therefore the performance index is below the lower limit of the reference area in that the check of the formula (7) has given a positive outcome, in a block 362 the automatic control 60 acts to increase the effort of the cyclist 64 with a slight decrease in the pedalling cadence by increasing the gear ratio. The controller 16 thus outputs the command increase_ratio.

Once the control signal or command increase_ratio has been output, or once such a command has been actuated in the gearshift 10, the timer relative to the sampling time period sampling_time is re-triggered in block 358, and the cycle ends, in block 360.

In the case in which the check of block 356 gives a positive outcome, and therefore the detected performance index is above the upper limit of the reference area in that the check of the formula (8) has given a positive outcome, the controller 16 must act to decrease the effort of the cyclist 64 and increase the pedalling cadence, by decreasing the gear ratio.

Preferably, if the relative option is enabled, before proceeding to output the related command decrease_ratio, the controller checks, in a block 364, whether the detected_heart_rate is above the anaerobic_threshold value, formula (2) above.

In the negative case, in a block 366 the controller 16 outputs the command decrease_ratio and proceeds with block 358 of re-triggering the sampling time period sampling_time, and with block 360 of exit from the procedure.

In the positive case, on the other hand, in a block 368 the ALARM state described above with reference to block 166 of FIG. 7 is entered. As stated there, the ALARM state can be activated when the formula (2) is satisfied for a predetermined minimum time period, so as to tolerate brief heart rate spikes.

Summarising, in the Performance Index Training mode, the innovative performance index preferably given by the ratio between the pedalling power and the heart rate is brought to the desired value through adjustment of the gear ratio, and the heart rate is not allowed to exceed the anaerobic threshold (except possibly for a sufficiently short time period).

As stated in the introductory part, the performance index performance_index can be a function of the heart rate of the cyclist and of the pedalling power different from the ratio indicated in formula (1).

In another alternative training mode, the reference value of the performance index performance_index_setpoint can vary over time. In particular it is possible to provide for a stepped progression analogous to the stepped progression of the reference value of the power in the Repetitions Training mode, illustrated in FIG. 6. The flow chart of such a training mode is within the capabilities of one skilled in the art in light of those shown in FIGS. 11 and 12 and described above.

Relative to the command increase_ratio according to blocks 212, 262, 330, 362 and to the command decrease_ratio according to blocks 216, 266, 334, 366 different possibilities are preferably provided for.

When both a front derailleur and a rear derailleur are provided, typically the increase in gear ratio can take place by moving the rear derailleur onto a toothed wheel with a smaller diameter/smaller number of teeth and/or by moving the front derailleur onto a toothed wheel with a larger diameter/larger number of teeth; the decrease in gear ratio can take place by moving the rear derailleur onto a toothed wheel with a larger diameter/larger number of teeth and/or by moving the front derailleur onto a toothed wheel with a smaller diameter/smaller number of teeth.

In the system 1, the front derailleur 14 may or may not be enabled, and by default it is not in order to avoid unbalancing the cyclist. This represents an inventive aspect per se, independently of other aspects described herein.

Moreover, preferably in the system 1 the display means 30 can comprise an alarm light to indicate when the front derailleur is enabled and/or to indicate gearshifting of the front derailleur 14 in progress.

For the same purpose an audible alarm signal can be emitted, for example through the beeper 31.

Moreover, preferably in the system 1 there is the possibility of choosing between two or more gearshifting modes. FIG. 13 depicts selection means 400 among:

a light gearshifting mode 402, wherein the gear ratio is changed into the closest one among those available—the immediately greater one or the immediately smaller one, respectively;

a medium gearshifting mode 404, wherein the gear ratio is changed into the second closest one among those available—the second greater one or the second smaller one, respectively;

a strong gearshifting mode 406, wherein the gear ratio is changed into the third closest one among those available—the third greater one or the third smaller one, respectively.

This represents an inventive aspect per se, independently of other aspects described herein.

By combining the two possibilities, of choosing the gearshifting mode and of enabling/disabling the front derailleur, six different possibilities of increasing the gear ratio and six different possibilities of decreasing the gear ratio are obtained.

FIG. 14 illustrates an embodiment of a flow chart relative to the implementation of the control signal control_signal, compare. block 164 of FIG. 7.

In a block 450 it is checked whether the control_signal is increase_ratio or decrease_ratio.

If the control_signal is increase_signal, in a block 452 it is checked whether the gearshifting mode is set at light mode; in the negative case in a block 454 it is checked whether the gearshifting mode is set at medium mode; in the negative case in a block 456 it is checked—even though redundantly, since blocks 452, 454, 456 are actually a "CASE" instruction—whether the gearshifting mode is set to strong mode.

In the case of a positive outcome of the check of one of blocks 452, 454, 456 it is checked, in a respective block 458, 460, 462, whether the front derailleur 14 is or is not enabled—of course, if such an option is provided for.

In the negative case, in a respective block 464, 466, 468 the rear derailleur 12 is moved by moving it respectively by one toothed wheel, by two toothed wheels or by three toothed wheels in the direction of the toothed wheels with a smaller diameter/smaller number of teeth. This is schematically indicated with the label "rear derailleur-i", with i variable between 1 and 3, with reference to the movement of i positions upwards of a pointer to a table of gear ratios. Analogous notations are used in the blocks described hereinafter, including the notation "+i" with reference to the movement of i positions downwards of the pointer to a table of gear ratios.

In the case of positive check of one of the blocks 458, 460, 462, in a respective block 470, 472, 474 the rear derailleur 12 is moved by moving it respectively by one toothed wheel, by two toothed wheels or by three toothed wheels in the direction of the toothed wheels with a smaller diameter/smaller number of teeth, and simultaneously the front derailleur 14 is moved by always moving it by one toothed wheel in the direction of the toothed wheels with a greater diameter/greater number of teeth.

If, on the other hand, in block 450 the control_signal is a decrease_ratio, in a block 482 it is checked whether the gearshifting mode is set to light mode; in the negative case in a block 484 it is checked whether the gearshifting mode is set at medium mode; in the negative case in a block 486 it is checked—even though redundantly, since blocks 482, 484, 486 are actually a "CASE" instruction—whether the gearshifting mode is set to strong mode.

In the case of a positive outcome of the check of one of blocks 482, 484, 486 it is checked, in a respective block 488, 490, 492, whether the front derailleur 14 is or is not enabled—of course, if such an option is provided for.

In the negative case, in a respective block 494, 496, 498 the rear derailleur 12 is moved by moving it respectively by one toothed wheel, by two toothed wheels or by three toothed wheels in the direction of the toothed wheels with a greater diameter/greater number of teeth.

In the case of positive check of blocks 488, 490, 492, in a respective block 500, 502, 504 the rear derailleur 12 is moved by moving it respectively by one toothed wheel, by two toothed wheels or by three toothed wheels in the direction of the toothed wheels with a greater diameter/greater number of teeth, and simultaneously the front derailleur 14 is moved by always moving it by one toothed wheel in the direction of the toothed wheels with a smaller diameter/smaller number of teeth.

As stated, in each of the blocks 464, 466, 468, 470, 472, 474, 494, 496, 498, 500, 502, 504 it is possible for example to refer to a look-up table containing all of the gear ratios made possible by all of the combinations of a specific toothed wheel associated with the hub of the rear wheel and a specific toothed wheel associated with the axle of the pedal cranks.

From each of the blocks 464, 466, 468, 470, 472, 474, 494, 496, 498, 500, 502, 504 one passes to an exit block 506.

It should be understood that the order of the various checks according to FIG. 14 can be any.

Those skilled in the art will understand that the aforementioned possibilities are reduced when the rear derailleur 12 and/or the front derailleur 14 is/are close to or at an extreme position, so that, for example, a toothed wheel with a greater diameter/greater number of teeth or a sufficient number of such toothed wheels is not present.

Moreover, the aforementioned possibilities can be deliberately reduced when it is wished to avoid the combinations of a specific toothed wheel associated with the hub of the rear wheel and a specific toothed wheel associated with the axle of the pedal cranks, for example those combinations that involve a very skew position of the chain.

FIG. 15 illustrates a more detailed flow chart relative to the Warm-up step, which is carried out by the controller 16 before the preselected training mode.

This cycle—as shall be seen—repeats at a preselected frequency, governed by the value of a predetermined timing period warm_up_sampling_time.

A suitable value for this predetermined timing period ranges from a few seconds to a few minutes. Preferably, warm_up_sampling_time is a variable the value of which is stored in the memory 17. Preferably, such a value can be modified by the user.

In a block 600 it is checked whether the sampling time period warm_up_sampling_time has elapsed, as indicated by the running out of a timer that had previously been triggered when the Warm-up step started.

If the sampling_time has not elapsed, the cycle ends in an exit block 602, to start again from block 600.

If, on the other hand, the sampling time has elapsed, in blocks 604, 606 it is checked whether the detected heart rate is in a predetermined "reference area", for example of width 2*Delta_Fc, about a set reference value training_heart_rate_setpoint, respectively checking the conditions:

$$\text{detected\_heart\_rate} < \text{training\_heart\_rate\_setpoint} - \text{Delta\_}Fc \qquad (9)$$

$$\text{detected\_heart\_rate} > \text{training\_heart\_rate\_setpoint} + \text{Delta\_}Fc \qquad (10)$$

A suitable value for the predetermined frequency threshold training_heart_rate_setpoint ranges from 90 to 120 bpm (beats per minute). Preferably, such a threshold is a variable the value of which is stored in the memory 17. Preferably, such a value can be modified by the user.

Preferably, the predetermined frequency threshold training_heart_rate_setpoint by default takes up a value equal to a predetermined percentage, more preferably equal to 75%, of the heart rate threshold corresponding to the "anaerobic threshold" anaerobic_threshold.

Therefore, preferably:

$$\text{training\_heart\_rate\_setpoint} = \text{anaerobic\_threshold} * K / 100 \quad (11)$$

and more preferably $$\text{training\_heart\_rate\_setpoint} = \text{anaerobic\_threshold} * 75\% \quad (12)$$

The "reference area" can for example be of a comparable size to the resolution of the heart rate monitor 34. In this way, the system 1 ignores very small differences, which could result in too frequent gearshifting. For example Delta_Fc can be 1 bpm.

The "reference area" does not necessarily have to be symmetrical about the set reference value training_heart_rate_setpoint, namely the values subtracted and added in formulae (9) and (10) do not necessarily have to be equal to each other.

In the case in which both of the blocks 604, 606 have a negative outcome, the timer relative to the sampling_time period warm_up_sampling_time is re-triggered in a block 608, and the cycle ends, in a block 610.

In the case in which block 604 has a positive outcome and therefore the detected heart rate is below the lower limit of the reference area in that the check of formula (9) has given a positive outcome, in a block 612 the automatic control 60 checks whether the heart rate of the cyclist is increasing, through the check of the formula $$\text{detected\_heart\_rate} > \text{previous\_heart\_rate} + \text{Delta\_Fc} \quad (13)$$

where previous_heart_rate was suitably initialized to the value of the detected_heart_rate at the start of the Warm-up mode.

In the negative case, wherein the heart rate is not increasing, the timer relative to the sampling_time period warm_up_sampling_time is re-triggered in block 608, and the cycle ends in block 610.

In the positive case, wherein the heart rate is increasing, the controller 16 acts to further increase the effort of the cyclist 64, by increasing the gear ratio, and thus in a block 614 outputs the command increase_ratio.

Thereafter, the timer relative to the sampling_time period warm_up_sampling_time is re-triggered in block 616, the value of the variable previous_heart_rate is updated to the current value detected_heart_rate in block 618, and the cycle ends in block 620.

In the case in which the check of block 606 gives a positive outcome, and therefore the detected_heart_rate is above the upper limit of the reference area in that the check of formula (10) has given a positive outcome, the warm-up step can end.

However, preferably, if the relative option is enabled, before proceeding to set the training mode, the controller checks, in a block 622, whether the detected heart rate is above the anaerobic threshold value, formula (2) above.

In the negative case, in a block 624 the controller 16 sets the training mode (which has been preselected beforehand or which is selected at that time) and proceeds with a block 626 of re-triggering of the timer relative to the sampling time period sampling_time to be used in the training mode (FIGS. 9-12), and with a block 628 of exit from the procedure.

If, on the other hand, in the check of block 622 it turns out that the detected heart rate is above the anaerobic threshold value, in a block 630 the ALARM state described above with reference to block 166 of FIG. 7 is entered. As stated there, the ALARM state can be activated when formula (2) is satisfied for a predetermined minimum time period, so as to tolerate brief heart rate spikes.

Summarising, in the Warm-up mode, the heart rate of the cyclist is brought to the training heart rate (or slightly above) by gradually increasing the gear ratio, and it is not allowed to exceed the anaerobic threshold (except possibly for a sufficiently short time period).

There can also be a maximum duration of the Warm-up step, for example 20 minutes.

FIG. 16 illustrates a more detailed flow chart relative to the Cool-down step, which is carried out by the controller 16 after the training mode.

This cycle—as shall be seen—repeats at a preselected frequency, governed by the value of a predetermined timing period cool_down_sampling_time.

A suitable value for this predetermined timing period ranges of a few seconds to a few minutes. Preferably, cool_down_sampling_time is a variable the value of which is stored in the memory 17. Preferably, such a value can be modified by the user.

In a block 650 it is checked whether the sampling_time period cool_down_sampling_time has elapsed, as indicated by the running out of a timer that has previously been triggered when the Cool-down step started.

If the sampling_time has not elapsed, the cycle ends in an exit block 652, to start again from block 650.

If, on the other hand, the sampling time has elapsed, in blocks 654, 656 it is checked whether the detected heart rate is in a predetermined "reference area", for example of width 2*Delta_Fc, about a set reference value training_heart_rate_setpoint, respectively checking the conditions (9) and (10).

The aforementioned considerations regarding the predetermined heart rate threshold training_heart_rate_setpoint and the relative "reference area" apply.

In the case in which both blocks 654, 656 have a negative outcome, the timer relative to the sampling time period cool_down_sampling_time is re-triggered in a block 658, and the cycle ends, in a block 660.

In the case in which block 654 has a positive outcome and therefore the detected_heart_rate is below the lower limit of the reference area in that the check of the formula (9) has given a positive outcome, the Cool-down step ends, for example with the setting of a suitable End of Cool-Down Step flag in a block 662, the timer relative to the sampling time period cool_down_sampling_time is re-triggered in block 658, and the cycle ends in block 660.

In the case in which the check of block 656 gives a positive outcome, and therefore the detected heart rate is above the upper limit of the reference area in that the check of the formula (10) has given a positive outcome, firstly the controller checks, in a block 664, whether the detected heart rate is above the anaerobic threshold value, formula (2) above.

If in the check of block 664 it turns out that the detected heart rate is above the anaerobic threshold value, in a block 666 the ALARM state described above with reference to block 166 of FIG. 7 is entered. As stated there, the ALARM state can be activated when formula (2) is satisfied for a predetermined minimum time period, so as to tolerate brief heart rate spikes.

If, on the other hand, in the check of block 664 it turn out that the detected heart rate is not above the anaerobic threshold value, in a block 668 the automatic control 60 checks whether the heart rate of the cyclist is decreasing, through the check of the formula $$\text{detected\_heart\_rate} < \text{previous\_heart\_rate} - \text{Delta}\_Fc \quad (14)$$

where previous_heart_rate was suitably initialized to the value of the detected_heart_rate at the start of the Cool-down mode.

In the negative case, wherein the heart rate is not decreasing, the timer relative to the sampling time period cool_down_sampling_time is re-triggered in block 670, and the cycle ends in block 672.

In the positive case, wherein the heart rate is decreasing, the controller 16 acts to further decrease the effort of the cyclist 64, by reducing the gear ratio, and therefore in a block 674 outputs the command decrease_ratio.

Thereafter, the timer relative to the sampling time period cool_down_sampling_time is re-triggered in block 676, the value of the variable previous_heart_rate is updated to the current value detected_heart_rate in block 678, and the cycle ends in block 680.

Summarising, in the Cool-down mode, the heart rate of the cyclist is brought below the training heart rate by gradually decreasing the gear ratio, and it is not allowed to exceed the anaerobic threshold (except possibly for a sufficiently short time period).

It is also possible to provide for a maximum duration of the Cool-down step, for example 15 minutes.

Also as far as blocks 614 and 674 of FIGS. 15 and 16 are concerned, what has been outlined with reference to FIGS. 13 and 14 applies. Preferably, in the Warm-up and Cool-down modes the light gearshifting mode 402 is used.

In the case in which there are other sensors besides the heart rate monitor 34 and the power sensor 36, it is possible to supplement the automatic control of the invention with further checks, so as to optimize the performance of the biomechanical system 62, taking better account of the physical characteristics of the athlete, the characteristics of the electro-mechanical part of the bicycle, and/or the characteristics of the travel route.

In the case in which there is a cadence sensor 38, it is possible to provide for enabling the actuation of the gearshiftings and/or the output of the control signal increase_ratio or decrease_ratio only if the chain is moving, so as not to damage the gearshift 10. In particular, it is possible to provide for enabling the actuation of the gearshiftings and/or the output of the control signal increase_ratio or decrease-ratio only if the cadence detected by such a cadence sensor 38 is equal or close to a respective setpoint, for example if it is within a range about the value cadence_setpoint, range which is definable as cadence_setpoint±q where q is a constant expressed in revolutions per minute, for example 5 revolutions/minute. A suitable value for the cadence setpoint is for example 60 revolutions/minute.

Moreover, providing for one or more sensors 32 in the system 1 allows a series of values acquired over time to be stored for their subsequent processing, for example to check whether for a given cyclist, a given route, a given type of paving etc. the gearshift 10 and in particular its toothed wheels and the available gear ratios are suitable. It is therefore possible to identify, especially in the field of competitive racing, the gearshift 10 that allows the best performance.

It is also possible to use such series of values acquired over time to evaluate the efficiency of the mechanical means and its deterioration over time.

The controller 16 preferably implements a setting mode in which the values of the various parameters/variables discussed above are set by the user, preferably each within a predetermined range of values. Moreover, preferably for each parameter/variable a default value to be used in the absence of a setting defined by the user is stored in a read only area of the memory 17.

The above is a description of various embodiments of inventive aspects, and further changes can be made without departing from the scope of the present invention. The shape and/or size and/or location and/or orientation of the various components and/or the sequence of the various steps can be changed. The functions of one element or module can be carried out by two or more components or modules, and vice-versa. Components shown directly connected or contacting each other may have intermediate structures arranged between them. Steps shown as directly subsequent can have intermediate steps carried out between them. The details shown in a figure and/or described with reference to a figure or to an embodiment can apply in other figures or embodiments. Not all of the details shown in a figure or described in a same context have to necessarily be present in a same embodiment. Features or aspects that turn out to be innovative with respect to the prior art, alone or in combination with other features, should be deemed to be described per se, independently of what is explicitly described as innovative.

What is claimed:

1. A method for actuating a bicycle electronic gearshift, comprising the steps of:
    a) receiving a signal indicative of a cyclist's heart rate while using the bicycle,
    b) receiving a signal indicative of power delivered by the cyclist,
    c) calculating a performance index as a function of the value of the signal indicative of the power and of the value of the signal indicative of the heart rate,
    d) obtaining a reference value for the performance index,
    e) comparing the calculated performance index with the reference value of the performance index,
    f) emitting a control signal, as a function of the outcome of comparing step e), to cause a gearshift to occur.

2. The method according to claim 1, wherein step c) comprises calculating the performance index as a ratio between the value of the signal indicative of the power and the value of the signal indicative of the heart rate.

3. The method according to claim 1, wherein step e) comprises checking whether the calculated performance index is below a lower limit of a reference area about the reference value of the performance index, and:
    in an affirmative case, step f) comprises emitting a signal to increase a gear ratio of the gearshift;
    in a negative case, step f) comprises emitting a signal to reduce a gear ratio of the gearshift.

4. The method according to claim 1, further comprising the step of:
    g) checking whether the value of the signal indicative of the cyclist's heart rate is above a threshold value indicative of the cyclist's anaerobic threshold, and wherein step f) of emitting a control signal is carried out only if the check of step g) has a negative outcome, while if the check of step g) has a positive outcome, the method comprises the step of:
  h) activating an alarm mode.

5. The method according to claim 4, wherein step h) of activating an alarm mode comprises emitting a signal to reduce a gear ratio of the gearshift.

6. The method according to claim 1, wherein steps a)-f) are carried out at a sampling frequency selectable from at least two different values.

7. The method according to claim 6, comprising the step of:
  i) a selecting the sampling frequency based on the signal indicative of the heart rate of the cyclist using the bicycle and/or on the signal indicative of the power delivered by the cyclist.

8. The method according to claim 1, wherein the bicycle electronic gearshift comprises a rear derailleur and a front derailleur, and the method further comprises the steps of:
  j) selectively enabling or disabling the movement of the front derailleur, and
  k) actuating the control signal through a movement of the rear derailleur and/or a movement of the front derailleur in the case in which the movement of the front derailleur is enabled in step j), through a movement of only the rear derailleur in the case in which the movement of the front derailleur is disabled in step j).

9. The method according to claim 8, further comprising the step of indicating to the cyclist when the front derailleur is enabled and/or indicating gearshifting of the front derailleur in progress.

10. The method according to claim 1, further comprising the steps of:
  l) receiving a gearshifting request signal from a user interface,
  m) in a semi-automatic mode, step f) comprises emitting a control signal as a function of the outcome of comparing step e) and/or based on the gearshifting request signal received in step l).

11. The method according to claim 10, wherein in a default mode, the control signal is emitted giving priority to the outcome of comparing step e).

12. The method according to claim 1, wherein step d) comprises:
  d1) generating the reference value for the performance index with a stepped progression.

13. The method according to claim 12, wherein step d1) comprises:
  d2) generating the reference value for the performance index with a stepped progression that repeats cyclically.

14. The method according to claim 1, comprising the step of:
  n) selecting from at least two gearshifting modes selected among a light gearshifting mode, a medium gearshifting mode, a strong gearshifting mode, and wherein
    if the preselected gearshifting mode is light gearshifting mode, step f) of emitting a control signal comprises emitting a request signal for changing the gear ratio into the closest one among those available—the immediately greater one or the immediately smaller one, respectively;
    if the preselected gearshifting mode is medium gearshifting mode, step f) of emitting a control signal comprises emitting a request signal for changing the gear ratio into the second closest one among those available—the second greater one or the second smaller one, respectively;
    if the preselected gearshifting mode is strong gearshifting mode, step f) of emitting a control signal comprises emitting a request signal for changing the gear ratio into the third closest one among those available—the third greater one or the third smaller one, respectively.

15. A bicycle electronic system comprising an electronic gearshift, a controller, a heart rate monitor, and a power sensor, wherein the controller is configured to carry out the steps of claim 1.

* * * * *